US006976990B2

(12) United States Patent
Mowry

(10) Patent No.: US 6,976,990 B2
(45) Date of Patent: Dec. 20, 2005

(54) INTRAVASCULAR VENTRICULOCORONARY BYPASS VIA A SEPTAL PASSAGEWAY

(75) Inventor: David H. Mowry, Eden Prairie, MN (US)

(73) Assignee: Percardia, Inc., Merrimack, NH (US)

( * ) Notice: Subject to any disclaimer, the term of this patent is extended or adjusted under 35 U.S.C. 154(b) by 637 days.

(21) Appl. No.: 09/769,746

(22) Filed: Jan. 25, 2001

(65) Prior Publication Data

US 2002/0099404 A1 Jul. 25, 2002

(51) Int. Cl.$^7$ .............................................. A61M 29/00
(52) U.S. Cl. ........................... 606/194; 606/7; 606/108; 604/96.01; 604/104; 623/1.11
(58) Field of Search ................ 606/1, 7, 108, 606/194, 195; 128/897, 898; 600/16–18; 604/96.01, 104; 623/1, 1.11, 11.11

(56) References Cited

U.S. PATENT DOCUMENTS

| 4,953,553 A | 9/1990 | Tremulis |
| 5,193,546 A | 3/1993 | Shaknovich |
| 5,254,113 A | 10/1993 | Wilk |
| 5,258,008 A | 11/1993 | Wilk |
| 5,287,861 A | 2/1994 | Wilk |

(Continued)

FOREIGN PATENT DOCUMENTS

| AU | 757647 | 2/2003 |
| EP | 0 515 867 A2 | 12/1992 |
| EP | 0 732 088 A2 | 9/1996 |
| EP | 0 815 798 A2 | 7/1997 |
| EP | 0 829 239 A1 | 8/1997 |

(Continued)

OTHER PUBLICATIONS

US 6,331,185, 12/2001, Gambale et al. (withdrawn)
Wakabayashi et al.; Myocardial boring for the ischemic heart; International Cardiovascular Society; vol. 95 (Nov. 1967) pp. 743–752.
Lary et al.; Myocardial revascularization experiments using the epicardium; Arch. Surg., vol. 98 (Jan. 1969) pp. 69–72.
Kuzela et al.; Experimental evaluation of direct transventricular revascularization; Journal of Thoracic and Cardiovascular Surgery, vol. 57 (Jan.–Jun. 1969) pp. 770–773.
Anabtawi et al.; Experimental evaluation of myocardial tunnelization as a method of myocardial revascularization; Journal of Thoracic and Cardiovascular Surgery, (Nov. 1969) pp. 638–646.
Palmaz et al.; Expandable intrahepatic portacaval shunt stents in dogs with chronic portal hypertension; AJR, vol. 147 (Dec. 1986) pp. 1251–1254.
Palmaz et al.; Expandable intrahepatic portacaval shunt stents: early experience in the dog; AJR, vol. 145 (Oct. 1985) pp. 821–825.
Gardner et al.; An experimental anatomic study of indirect myocardial revascularization; Journal of Surgical Research, vol. 11 (1971) pp. 243–247.
Lary et al., A method for creating a coronary–myocardial artery; Surgery, vol. 59 (Jun. 1966) pp. 1061–10640.
Ahmed et al.; Silent left coronary artery–cameral fistula: probable cause of myocardial ischemia; American Heart Journal, vol. 104 (Oct. 1982) pp. 869–870.

(Continued)

*Primary Examiner*—Henry Bennett
*Assistant Examiner*—Andrea M. Ragonese
(74) *Attorney, Agent, or Firm*—Finnegan, Henderson, Farabow, Garrett & Dunner LLP

(57) ABSTRACT

A method for performing a bypass procedure utilizes the patient's vascular system for accessing or reaching a desired location within the patient's body. The method may also provide a direct flow path from a heart chamber to a coronary vessel via a septal passageway.

25 Claims, 18 Drawing Sheets

U.S. PATENT DOCUMENTS

| | | | |
|---|---|---|---|
| 5,330,486 A | 7/1994 | Wilk | |
| 5,344,426 A | 9/1994 | Lau et al. | |
| 5,385,528 A | 1/1995 | Wilk | |
| 5,389,096 A | 2/1995 | Aita et al. | |
| 5,409,019 A | 4/1995 | Wilk | |
| 5,425,757 A | 6/1995 | Tiefenbrun et al. | |
| 5,425,765 A | 6/1995 | Tiefenbrun et al. | |
| 5,429,144 A | 7/1995 | Wilk | |
| 5,470,320 A | 11/1995 | Tiefenbrun et al. | |
| 5,554,119 A | 9/1996 | Harrison et al. | |
| 5,593,434 A | 1/1997 | Williams | |
| 5,618,299 A | 4/1997 | Khosravi et al. | |
| 5,662,124 A | 9/1997 | Wilk | |
| 5,733,267 A | 3/1998 | Del Toro | |
| 5,755,682 A | 5/1998 | Knudson et al. | |
| 5,758,663 A | 6/1998 | Wilk et al. | |
| 5,800,334 A | 9/1998 | Wilk | |
| 5,807,384 A | 9/1998 | Mueller | |
| 5,810,836 A | 9/1998 | Hussein et al. | |
| 5,824,071 A | 10/1998 | Nelson et al. | |
| 5,830,222 A | 11/1998 | Makower | |
| 5,876,373 A | 3/1999 | Giba et al. | |
| 5,878,751 A | 3/1999 | Hussein et al. | |
| 5,885,259 A | 3/1999 | Berg | |
| 5,908,028 A | 6/1999 | Wilk | |
| 5,908,029 A | 6/1999 | Knudson et al. | |
| 5,922,022 A | 7/1999 | Nash et al. | |
| 5,925,012 A | 7/1999 | Murphy-Chutorian et al. | |
| 5,931,848 A | 8/1999 | Saadat | |
| 5,935,161 A | 8/1999 | Robinson et al. | |
| 5,938,632 A | 8/1999 | Ellis | |
| 5,944,019 A | 8/1999 | Knudson et al. | |
| 5,968,064 A | 10/1999 | Selmon et al. | |
| 5,971,911 A | 10/1999 | Wilk | |
| 5,971,993 A | 10/1999 | Hussein et al. | |
| 5,976,155 A | 11/1999 | Foreman et al. | |
| 5,980,533 A | 11/1999 | Holman | |
| 5,980,548 A | 11/1999 | Evans et al. | |
| 5,984,956 A | 11/1999 | Tweden et al. | |
| 5,997,525 A | 12/1999 | March et al. | |
| 5,999,678 A | 12/1999 | Murphy-Chutorian et al. | |
| 6,004,261 A | 12/1999 | Sinofsky et al. | |
| 6,004,347 A | 12/1999 | McNamara et al. | |
| 6,007,543 A | 12/1999 | Ellis et al. | |
| 6,010,449 A | 1/2000 | Selmon et al. | |
| 6,026,814 A | 2/2000 | LaFontaine et al. | |
| 6,029,672 A | 2/2000 | Vanney et al. | |
| 6,035,856 A | 3/2000 | LaFontaine et al. | |
| 6,036,677 A | 3/2000 | Javier, Jr. et al. | |
| 6,036,697 A | 3/2000 | DiCaprio | |
| 6,045,565 A | 4/2000 | Ellis et al. | |
| 6,053,924 A | 4/2000 | Hussein | |
| 6,053,942 A | 4/2000 | Eno et al. | |
| 6,056,743 A | 5/2000 | Ellis et al. | |
| 6,067,988 A | 5/2000 | Mueller | |
| 6,068,638 A | 5/2000 | Makower | |
| 6,071,292 A | 6/2000 | Makower et al. | |
| 6,076,529 A | 6/2000 | Vanney et al. | |
| 6,080,163 A | 6/2000 | Hussein et al. | |
| 6,080,170 A | 6/2000 | Nash et al. | |
| 6,090,063 A | 7/2000 | Makower et al. | |
| 6,092,526 A | 7/2000 | LaFontaine et al. | |
| 6,093,166 A | 7/2000 | Knudson et al. | |
| 6,093,177 A | 7/2000 | Javier, Jr. et al. | |
| 6,093,185 A | 7/2000 | Ellis et al. | |
| 6,102,941 A | 8/2000 | Tweden et al. | |
| 6,113,630 A | 9/2000 | Vanney et al. | |
| 6,113,823 A | 9/2000 | Eno | |
| 6,120,520 A | 9/2000 | Saadat et al. | |
| 6,123,682 A | 9/2000 | Knudson et al. | |
| 6,126,649 A | 10/2000 | VanTassel et al. | |
| 6,126,654 A | 10/2000 | Giba et al. | |
| 6,132,451 A | 10/2000 | Payne et al. | |
| 6,139,541 A | 10/2000 | Vanney et al. | |
| 6,155,264 A | 12/2000 | Ressemann et al. | |
| 6,155,968 A | 12/2000 | Wilk | |
| 6,156,031 A | 12/2000 | Aita et al. | |
| 6,157,852 A | 12/2000 | Selmon et al. | |
| 6,159,225 A | 12/2000 | Makower | |
| 6,165,185 A | 12/2000 | Shennib et al. | |
| 6,165,188 A | 12/2000 | Saadat et al. | |
| 6,171,251 B1 | 1/2001 | Mueller et al. | |
| 6,182,668 B1 | 2/2001 | Tweden et al. | |
| 6,186,972 B1 | 2/2001 | Nelson et al. | |
| 6,190,353 B1 | 2/2001 | Makower et al. | |
| 6,193,726 B1 | 2/2001 | Vanney | |
| 6,193,734 B1 | 2/2001 | Bolduc et al. | |
| D438,618 S | 3/2001 | Solem | |
| 6,196,230 B1 | 3/2001 | Hall et al. | |
| 6,197,050 B1 | 3/2001 | Eno et al. | |
| 6,197,324 B1 | 3/2001 | Crittenden | |
| 6,200,311 B1 | 3/2001 | Danek et al. | |
| 6,203,556 B1 | 3/2001 | Evans et al. | |
| 6,213,126 B1 | 4/2001 | LaFontaine et al. | |
| 6,214,041 B1 | 4/2001 | Tweden et al. | |
| 6,217,527 B1 | 4/2001 | Selmon et al. | |
| 6,217,549 B1 | 4/2001 | Selmon et al. | |
| 6,217,575 B1 | 4/2001 | DeVore et al. | |
| 6,221,049 B1 | 4/2001 | Selmon et al. | |
| 6,223,752 B1 | 5/2001 | Vanney et al. | |
| 6,224,584 B1 | 5/2001 | March et al. | |
| 6,231,546 B1 | 5/2001 | Milo et al. | |
| 6,231,551 B1 | 5/2001 | Barbut | |
| 6,231,587 B1 | 5/2001 | Makower | |
| 6,235,000 B1 | 5/2001 | Milo et al. | |
| 6,237,607 B1 | 5/2001 | Vanney et al. | |
| 6,238,406 B1 | 5/2001 | Ellis et al. | |
| 6,241,667 B1 | 6/2001 | Vetter et al. | |
| 6,248,112 B1 | 6/2001 | Gambale et al. | |
| 6,250,305 B1 | 6/2001 | Tweden | |
| 6,251,079 B1 | 6/2001 | Gambale et al. | |
| 6,251,104 B1 | 6/2001 | Kesten et al. | |
| 6,251,116 B1 | 6/2001 | Shennib et al. | |
| 6,251,418 B1 | 6/2001 | Ahern et al. | |
| 6,253,768 B1 | 7/2001 | Wilk | |
| 6,253,769 B1 | 7/2001 | LaFontaine et al. | |
| 6,254,564 B1 | 7/2001 | Wilk et al. | |
| 6,258,021 B1 | 7/2001 | Wilk | |
| 6,258,052 B1 | 7/2001 | Milo | |
| 6,258,119 B1 | 7/2001 | Hussein et al. | |
| 6,261,304 B1 | 7/2001 | Hall et al. | |
| 6,283,951 B1 | 9/2001 | Flaherty et al. | |
| 6,283,983 B1 | 9/2001 | Makower et al. | |
| 6,285,903 B1 | 9/2001 | Rosenthal et al. | |
| 6,287,317 B1 | 9/2001 | Makower et al. | |
| 6,290,709 B1 | 9/2001 | Ellis et al. | |
| 6,290,728 B1 | 9/2001 | Phelps et al. | |
| 6,302,685 B1 | 10/2001 | Lobel et al. | |
| 6,302,875 B1 | 10/2001 | Makower et al. | |
| 6,302,892 B1 | 10/2001 | Wilk | |
| 6,322,548 B1 | 11/2001 | Payne et al. | |
| 6,330,884 B1 | 12/2001 | Kim | |
| 6,344,027 B1 | 2/2002 | Goll | |
| 6,350,248 B1 | 2/2002 | Knudson et al. | |
| 6,352,543 B1 | 3/2002 | Cole | |
| 6,361,519 B1 | 3/2002 | Knudson et al. | |
| 6,363,938 B2 | 4/2002 | Saadat et al. | |
| 6,363,939 B1 | 4/2002 | Wilk | |
| 6,375,615 B1 | 4/2002 | Flaherty et al. | |
| 6,379,319 B1 | 4/2002 | Garibotto et al. | |
| 6,387,119 B2 | 5/2002 | Wolf et al. | |

| Patent No. | Date | Inventor(s) |
|---|---|---|
| 6,390,098 B1 | 5/2002 | LaFontaine et al. |
| 6,395,208 B1 | 5/2002 | Herweck et al. |
| 6,402,740 B1 | 6/2002 | Ellis et al. |
| 6,406,488 B1 | 6/2002 | Tweden et al. |
| 6,406,491 B1 | 6/2002 | Vanney |
| 6,409,697 B2 | 6/2002 | Eno et al. |
| 6,409,751 B1 | 6/2002 | Hall et al. |
| 6,416,490 B1 | 7/2002 | Ellis et al. |
| 6,423,089 B1 | 7/2002 | Gingras et al. |
| 6,432,119 B1 | 8/2002 | Saadat |
| 6,432,126 B1 | 8/2002 | Gambale et al. |
| 6,432,127 B1 | 8/2002 | Kim et al. |
| 6,432,132 B1 | 8/2002 | Cottone et al. |
| 6,443,158 B1 | 9/2002 | LaFontaine et al. |
| 6,447,522 B2 | 9/2002 | Gambale et al. |
| 6,447,539 B1 | 9/2002 | Nelson et al. |
| 6,454,760 B2 | 9/2002 | Vanney |
| 6,454,794 B1 | 9/2002 | Knudson et al. |
| 6,458,092 B1 | 10/2002 | Gambale et al. |
| 6,458,140 B2 | 10/2002 | Akin et al. |
| 6,458,323 B1 | 10/2002 | Boekstegers |
| 6,464,709 B1 | 10/2002 | Shennib et al. |
| 6,475,226 B1 | 11/2002 | Belef et al. |
| 6,475,244 B2 | 11/2002 | Herweck et al. |
| 6,482,220 B1 | 11/2002 | Mueller |
| 6,491,689 B1 | 12/2002 | Ellis et al. |
| 6,491,707 B2 | 12/2002 | Makower et al. |
| 6,506,408 B1 | 1/2003 | Palasis |
| 6,508,824 B1 | 1/2003 | Flaherty |
| 6,508,825 B1 | 1/2003 | Selmon et al. |
| 6,511,458 B2 | 1/2003 | Milo et al. |
| 6,514,217 B1 | 2/2003 | Selmon et al. |
| 6,514,271 B2 | 2/2003 | Evans et al. |
| 6,517,527 B2 | 2/2003 | Gambale et al. |
| 6,517,558 B2 | 2/2003 | Gittings et al. |
| 6,524,323 B1 | 2/2003 | Nash et al. |
| 6,524,324 B1 | 2/2003 | Mueller et al. |
| 6,530,914 B1 | 3/2003 | Mickley |
| 6,533,779 B2 | 3/2003 | Kinsella et al. |
| 6,544,230 B1 | 4/2003 | Flaherty et al. |
| 6,559,132 B1 | 5/2003 | Holmer |
| 6,561,998 B1 | 5/2003 | Roth et al. |
| 6,565,528 B1 | 5/2003 | Mueller |
| 6,565,594 B1 | 5/2003 | Herweck et al. |
| 6,569,145 B1 | 5/2003 | Shmulewitz et al. |
| 6,569,147 B1 | 5/2003 | Evans et al. |
| 6,573,311 B1 | 6/2003 | Martakos et al. |
| 6,575,168 B2 | 6/2003 | LaFontaine et al. |
| 6,579,311 B1 | 6/2003 | Makower |
| 6,582,444 B2 | 6/2003 | Wilk |
| 6,582,463 B1 | 6/2003 | Mowry et al. |
| 6,585,650 B1 | 7/2003 | Solem |
| 6,587,718 B2 | 7/2003 | Talpade |
| 6,589,164 B1 | 7/2003 | Flaherty |
| 6,599,304 B1 | 7/2003 | Selmon et al. |
| 6,602,241 B2 | 8/2003 | Makower et al. |
| 6,605,053 B1 | 8/2003 | Kamm et al. |
| 6,605,113 B2 | 8/2003 | Wilk |
| 6,610,100 B2 | 8/2003 | Phelps et al. |
| 6,613,026 B1 | 9/2003 | Palasis et al. |
| 6,613,081 B2 | 9/2003 | Kim et al. |
| 6,616,626 B2 | 9/2003 | Crank et al. |
| 6,616,675 B1 | 9/2003 | Evard et al. |
| 6,635,214 B2 | 10/2003 | Rapacki et al. |
| 6,638,237 B1 | 10/2003 | Guiles et al. |
| 6,638,247 B1 | 10/2003 | Selmon et al. |
| 6,638,293 B1 | 10/2003 | Makower et al. |
| 6,641,610 B2 | 11/2003 | Wolf et al. |
| 6,651,670 B2 | 11/2003 | Rapacki et al. |
| 6,652,540 B1 | 11/2003 | Cole et al. |
| 6,652,546 B1 | 11/2003 | Nash et al. |
| 6,655,386 B1 | 12/2003 | Makower et al. |
| 6,660,003 B1 | 12/2003 | DeVore et al. |
| 6,660,024 B1 | 12/2003 | Flaherty et al. |
| 6,669,691 B1 | 12/2003 | Taimisto |
| 6,669,709 B1 | 12/2003 | Cohn et al. |
| 6,685,648 B2 | 2/2004 | Flaherty et al. |
| 6,685,716 B1 | 2/2004 | Flaherty et al. |
| 6,694,983 B2 | 2/2004 | Wolf et al. |
| 6,709,425 B2 | 3/2004 | Gambale et al. |
| 6,709,427 B1 | 3/2004 | Nash et al. |
| 6,709,444 B1 | 3/2004 | Makower |
| 6,719,770 B2 | 4/2004 | Laufer et al. |
| 2001/0000041 A1 | 3/2001 | Selmon et al. |
| 2001/0003985 A1 | 6/2001 | Lafontaine et al. |
| 2001/0004683 A1 | 6/2001 | Gambale et al. |
| 2001/0004690 A1 | 6/2001 | Gambale et al. |
| 2001/0004699 A1 | 6/2001 | Gittings et al. |
| 2001/0008969 A1 | 7/2001 | Evans et al. |
| 2001/0012924 A1 | 8/2001 | Milo et al. |
| 2001/0012948 A1 | 8/2001 | Vanney |
| 2001/0014813 A1 | 8/2001 | Saadat et al. |
| 2001/0016700 A1 | 8/2001 | Eno et al. |
| 2001/0018596 A1 | 8/2001 | Selmon et al. |
| 2001/0020172 A1 | 9/2001 | Selmon et al. |
| 2001/0025643 A1 | 10/2001 | Foley |
| 2001/0027287 A1 | 10/2001 | Shmulewitz et al. |
| 2001/0029385 A1 | 10/2001 | Shennib et al. |
| 2001/0034547 A1 | 10/2001 | Hall et al. |
| 2001/0037117 A1 | 11/2001 | Gambale et al. |
| 2001/0037149 A1 | 11/2001 | Wilk |
| 2001/0039426 A1 | 11/2001 | Makower et al. |
| 2001/0039445 A1 | 11/2001 | Hall et al. |
| 2001/0041902 A1 | 11/2001 | Lepulu et al. |
| 2001/0044631 A1 | 11/2001 | Akin et al. |
| 2001/0047165 A1 | 11/2001 | Makower et al. |
| 2001/0047197 A1 | 11/2001 | Foley |
| 2001/0049523 A1 | 12/2001 | DeVore et al. |
| 2001/0053932 A1 | 12/2001 | Phleps et al. |
| 2002/0002349 A1 | 1/2002 | Flaherty et al. |
| 2002/0004662 A1 | 1/2002 | Wilk |
| 2002/0004663 A1 | 1/2002 | Gittings et al. |
| 2002/0007138 A1 | 1/2002 | Wilk et al. |
| 2002/0029079 A1 | 3/2002 | Kim et al. |
| 2002/0032476 A1 | 3/2002 | Gambale et al. |
| 2002/0032478 A1 | 3/2002 | Boekstegers et al. |
| 2002/0033180 A1 | 3/2002 | Solem |
| 2002/0045928 A1 | 4/2002 | Boekstegers |
| 2002/0049486 A1 | 4/2002 | Knudson et al. |
| 2002/0049495 A1 | 4/2002 | Kutryk et al. |
| 2002/0058897 A1 | 5/2002 | Renati |
| 2002/0062146 A1 | 5/2002 | Makiwer et al. |
| 2002/0065478 A1 | 5/2002 | Knudson et al. |
| 2002/0072699 A1 | 6/2002 | Knudson et al. |
| 2002/0072758 A1 | 6/2002 | Reo et al. |
| 2002/0077566 A1 | 6/2002 | Laroya et al. |
| 2002/0077654 A1 | 6/2002 | Javier, Jr. et al. |
| 2002/0082546 A1 | 6/2002 | Crank et al. |
| 2002/0092535 A1 | 7/2002 | Wilk |
| 2002/0092536 A1 | 7/2002 | LaFontaine et al. |
| 2002/0095110 A1 | 7/2002 | Vanney et al. |
| 2002/0095111 A1 | 7/2002 | Tweden et al. |
| 2002/0095206 A1 | 7/2002 | Addonizio et al. |
| 2002/0099392 A1 | 7/2002 | Mowry et al. |
| 2002/0100484 A1 | 8/2002 | Hall et al. |
| 2002/0103459 A1 | 8/2002 | Sparks et al. |
| 2002/0103495 A1 | 8/2002 | Cole |
| 2002/0103534 A1 | 8/2002 | Vanney et al. |
| 2002/0111672 A1 | 8/2002 | Kim et al. |
| 2002/0123698 A1 | 9/2002 | Garibotto et al. |
| 2002/0138087 A1 | 9/2002 | Shennib et al. |
| 2002/0143285 A1 | 10/2002 | Eno et al. |

| | | | | | | | |
|---|---|---|---|---|---|---|---|
| 2002/0143289 | A1 | 10/2002 | Ellis et al. | GB | 2 316 322 B | | 2/1998 |
| 2002/0143347 | A1 | 10/2002 | Cole et al. | RU | 2026640 | | 1/1995 |
| 2002/0144696 | A1 | 10/2002 | Sharkawry et al. | SU | 1754128 | A1 | 8/1992 |
| 2002/0161383 | A1 | 10/2002 | Akin et al. | WO | WO 93/00868 | | 1/1993 |
| 2002/0161424 | A1 | 10/2002 | Rapacki et al. | WO | WO 95/35065 | | 12/1995 |
| 2002/0165479 | A1 | 11/2002 | Wilk | WO | WO 96/00033 | | 1/1996 |
| 2002/0165606 | A1 | 11/2002 | Wolf et al. | WO | WO 96/04854 | | 2/1996 |
| 2002/0179098 | A1 | 12/2002 | Makower et al. | WO | WO 96/05773 | | 2/1996 |
| 2002/0183716 | A1 | 12/2002 | Herweck et al. | WO | WO 96/32972 | | 10/1996 |
| 2002/0193782 | A1 | 12/2002 | Ellis et al. | WO | WO 96/35469 | | 11/1996 |
| 2003/0015816 | A1 | 1/2003 | Rapacki et al. | WO | WO 96/39962 | | 12/1996 |
| 2003/0018379 | A1 | 1/2003 | Knudson et al. | WO | WO 96/39964 | | 12/1996 |
| 2003/0044315 | A1 | 3/2003 | Boekstegers | WO | WO 96/39965 | | 12/1996 |
| 2003/0045828 | A1 | 3/2003 | Wilk | WO | WO 97/13463 | | 4/1997 |
| 2003/0055371 | A1 | 3/2003 | Wilk et al. | WO | WO 97/13471 | | 4/1997 |
| 2003/0062650 | A1 | 4/2003 | Martakos et al. | WO | WO 97/27893 | | 8/1997 |
| 2003/0073973 | A1 | 4/2003 | Evans et al. | WO | WO 97/27897 | | 8/1997 |
| 2003/0078561 | A1 | 4/2003 | Gambale et al. | WO | WO 97/27898 | | 8/1997 |
| 2003/0078562 | A1 | 4/2003 | Makower et al. | WO | WO 97/32551 | | 9/1997 |
| 2003/0097172 | A1 | 5/2003 | Shalev et al. | WO | WO 97/43961 | | 11/1997 |
| 2003/0100920 | A1 | 5/2003 | Akin et al. | WO | WO 98/03118 | | 1/1998 |
| 2003/0105514 | A1 | 6/2003 | Phelps et al. | WO | WO 98/06356 | | 2/1998 |
| 2003/0114872 | A1 | 6/2003 | Mueller et al. | WO | WO 98/08456 | | 3/1998 |
| 2003/0120195 | A1 | 6/2003 | Milo et al. | WO | WO 98/10714 | | 3/1998 |
| 2003/0120259 | A1 | 6/2003 | Mickley | WO | WO 98/16161 | | 4/1998 |
| 2003/0149474 | A1 | 8/2003 | Becker | WO | WO 98/24373 | | 6/1998 |
| 2003/0158573 | A1 | 8/2003 | Gittings et al. | WO | WO 98/25533 | | 6/1998 |
| 2003/0181938 | A1 | 9/2003 | Roth et al. | WO | WO 98/38916 | | 9/1998 |
| 2003/0191449 | A1 | 10/2003 | Nash et al. | WO | WO 98/38925 | | 9/1998 |
| 2003/0195457 | A1 | 10/2003 | LaFontaine et al. | WO | WO 98/38939 | | 9/1998 |
| 2003/0195458 | A1 | 10/2003 | Phelps et al. | WO | WO 98/38941 | | 9/1998 |
| 2003/0195606 | A1 | 10/2003 | Davidson et al. | WO | WO 98/39038 | | 9/1998 |
| 2003/0204160 | A1 | 10/2003 | Kamm et al. | WO | WO 98/46115 | | 10/1998 |
| 2003/0212413 | A1 | 11/2003 | Wilk | WO | WO 98/46119 | | 10/1998 |
| 2003/0216679 | A1 | 11/2003 | Wolf et al. | WO | WO 98/49964 | | 11/1998 |
| 2003/0229366 | A1 | 12/2003 | Reggie et al. | WO | WO 98/57590 | | 12/1998 |
| 2003/0236542 | A1 | 12/2003 | Makower | WO | WO 98/57591 | | 12/1998 |
| 2004/0006298 | A1 | 1/2004 | Wilk | WO | WO 98/57592 | | 12/1998 |
| 2004/0006301 | A1 | 1/2004 | Sell et al. | WO | WO 99/07296 | | 2/1999 |
| 2004/0015225 | A1 | 1/2004 | Kim et al. | WO | WO 99/08624 | | 2/1999 |
| 2004/0019348 | A1 | 1/2004 | Stevens et al. | WO | WO 99/15220 | | 4/1999 |
| 2004/0044392 | A1 | 3/2004 | Von Oepen | WO | WO 99/17671 | | 4/1999 |
| 2004/0059280 | A1 | 3/2004 | Makower et al. | WO | WO 99/17683 | | 4/1999 |
| 2004/0073157 | A1 | 4/2004 | Knudson et al. | WO | WO 99/21490 | | 5/1999 |
| 2004/0073238 | A1 | 4/2004 | Makower | WO | WO 99/21510 | | 5/1999 |
| 2004/0077987 | A1 | 4/2004 | Rapacki et al. | WO | WO 99/22655 | | 5/1999 |
| 2004/0077988 | A1 | 4/2004 | Tweden et al. | WO | WO 99/22658 | | 5/1999 |
| 2004/0077990 | A1 | 4/2004 | Knudson et al. | WO | WO 99/25273 | | 5/1999 |
| 2004/0092976 | A1 | 5/2004 | Mowry et al. | WO | WO 99/27985 | | 6/1999 |
| | | | | WO | WO 99/35977 | | 7/1999 |
| | | FOREIGN PATENT DOCUMENTS | | WO | WO 99/35979 | | 7/1999 |
| EP | 0 792 624 A1 | 9/1997 | | WO | WO 99/35980 | | 7/1999 |
| EP | 0 797 957 A1 | 10/1997 | | WO | WO 99/36000 | | 7/1999 |
| EP | 0 797 958 A1 | 10/1997 | | WO | WO 99/36001 | | 7/1999 |
| EP | 0 799 604 A1 | 10/1997 | | WO | WO 99/38459 | | 8/1999 |
| EP | 0 801 928 A1 | 10/1997 | | WO | WO 99/40853 | | 8/1999 |
| EP | 0 836 834 A2 | 10/1997 | | WO | WO 99/40868 | | 8/1999 |
| EP | 0 876 796 A2 | 5/1998 | | WO | WO 99/40963 | | 8/1999 |
| EP | 0 853 921 A2 | 7/1998 | | WO | WO 99/44524 | | 9/1999 |
| EP | 0 858 779 A1 | 8/1998 | | WO | WO 99/48545 | | 9/1999 |
| EP | 0 876 803 A2 | 11/1998 | | WO | WO 99/48549 | | 9/1999 |
| EP | 0 888 750 A1 | 1/1999 | | WO | WO 99/49793 | | 10/1999 |
| EP | 0 895 752 A1 | 2/1999 | | WO | WO 99/49910 | | 10/1999 |
| EP | 0 934 728 A2 | 8/1999 | | WO | WO 99/51162 | | 10/1999 |
| EP | 1 020 166 A1 | 7/2000 | | WO | WO 99/53863 | | 10/1999 |
| EP | 1 027 870 A1 | 8/2000 | | WO | WO 99/55406 | | 11/1999 |
| EP | 1 088 564 A1 | 4/2001 | | WO | WO 99/60941 | | 12/1999 |
| EP | 1 097 676 A1 | 5/2001 | | WO | WO 99/62430 | | 12/1999 |
| EP | 1 166 721 A2 | 1/2002 | | WO | WO 00/09195 | | 2/2000 |
| EP | 0 959 815 A1 | 12/2002 | | WO | WO 00/12029 | | 3/2000 |
| EP | 1 112 097 A1 | 6/2003 | | WO | WO 00/13722 | | 3/2000 |

| | | |
|---|---|---|
| WO | WO 00/15146 | 3/2000 |
| WO | WO 00/15147 | 3/2000 |
| WO | WO 00/15148 | 3/2000 |
| WO | WO 00/15149 A1 | 3/2000 |
| WO | WO 00/15275 | 3/2000 |
| WO | WO 00/18302 | 4/2000 |
| WO | WO 00/18323 | 4/2000 |
| WO | WO 00/18325 | 4/2000 |
| WO | WO 00/18326 | 4/2000 |
| WO | WO 00/18331 | 4/2000 |
| WO | WO 00/18462 | 4/2000 |
| WO | WO 00/21436 | 4/2000 |
| WO | WO 00/21461 | 4/2000 |
| WO | WO 00/21463 | 4/2000 |
| WO | WO 00/24449 | 5/2000 |
| WO | WO 00/33725 | 6/2000 |
| WO | WO 00/35376 | 6/2000 |
| WO | WO 00/36997 | 6/2000 |
| WO | WO 00/41632 | 7/2000 |
| WO | WO 00/41633 | 7/2000 |
| WO | WO 00/43051 | 7/2000 |
| WO | WO 00/45711 | 8/2000 |
| WO | WO 00/45886 | 8/2000 |
| WO | WO 00/49952 | 8/2000 |
| WO | WO 00/49954 | 8/2000 |
| WO | WO 00/49956 | 8/2000 |
| WO | WO 00/54660 | 9/2000 |
| WO | WO 00/54661 | 9/2000 |
| WO | WO 00/56224 | 9/2000 |
| WO | WO 00/56225 | 9/2000 |
| WO | WO 00/56387 | 9/2000 |
| WO | WO 00/66007 | 11/2000 |
| WO | WO 00/66009 | 11/2000 |
| WO | WO 00/66035 | 11/2000 |
| WO | WO 00/69345 | 11/2000 |
| WO | WO 00/69504 | 11/2000 |
| WO | WO 00/71195 A1 | 11/2000 |
| WO | WO 01/08566 A1 | 2/2001 |
| WO | WO 01/08602 A1 | 2/2001 |
| WO | WO 01/10340 A1 | 2/2001 |
| WO | WO 01/10341 A2 | 2/2001 |
| WO | WO 01/10347 A1 | 2/2001 |
| WO | WO 01/10348 A1 | 2/2001 |
| WO | WO 01/10349 A1 | 2/2001 |
| WO | WO 01/10350 A1 | 2/2001 |
| WO | WO 01/17440 A1 | 3/2001 |
| WO | WO 01/17456 A1 | 3/2001 |
| WO | WO 01/23016 A1 | 4/2001 |
| WO | WO 01/41657 A1 | 6/2001 |
| WO | WO 01/49187 A1 | 7/2001 |
| WO | WO 01/68158 A1 | 9/2001 |
| WO | WO 01/70133 A1 | 9/2001 |
| WO | WO 01/72239 A2 | 10/2001 |
| WO | WO 01/78801 A2 | 10/2001 |
| WO | WO 01/82803 A1 | 11/2001 |
| WO | WO 01/82837 A2 | 11/2001 |
| WO | WO 02/011647 A2 | 2/2002 |
| WO | WO 02/011807 A2 | 2/2002 |
| WO | WO 02/013698 A1 | 2/2002 |
| WO | WO 02/013699 A1 | 2/2002 |
| WO | WO 02/013703 A1 | 2/2002 |
| WO | WO 02/013704 A1 | 2/2002 |
| WO | WO 02/024108 A2 | 3/2002 |
| WO | WO 02/024247 A1 | 3/2002 |
| WO | WO 02/024248 A1 | 3/2002 |
| WO | WO 02/026310 A1 | 4/2002 |
| WO | WO 02/026462 A1 | 4/2002 |
| WO | WO 02/030325 A2 | 4/2002 |
| WO | WO 02/030326 A2 | 4/2002 |
| WO | WO 02/030330 A2 | 4/2002 |
| WO | WO 02/032330 A2 | 4/2002 |
| WO | WO 02/034323 A2 | 5/2002 |
| WO | WO 02/045598 A2 | 6/2002 |
| WO | WO 02/049695 A2 | 6/2002 |
| WO | WO 02/056937 A2 | 7/2002 |
| WO | WO 02/058567 A2 | 8/2002 |
| WO | WO 03/008005 A2 | 1/2003 |
| WO | WO 03/017870 A1 | 3/2003 |

OTHER PUBLICATIONS

Zemel et al.; Percutaneous transjugular portosystemic shunt; JAMA, vol. 266 (Jul. 1991) pp. 390–393.

Richter et al.; Transjugular intrahepatic portacaval stent shunt: preliminary clinical results; RSNA–SCVIR, vol. 174 (Mar. 1990) pp. 1027–1030.

Angell et al., Organ viability with hypothermia, The Journal of Thoracic and Cardiovascular Surgery, vol. 58, No. 5 (Nov. 1969) pp. 619–646.

Massimo et al., Myocardial, Revascularization by a New Method of Carrying Blood Directly from the left ventricular cavity into the Coronary Circulation., from the S. Maria.N-uova Hospital: Surgeon–in–Chief, Tominiaso Greco, M.D., received for publication Oct. 16, 1956, J. Thoracic Surgery vol. 34: (1957) pp. 257–264.

Archie, Joseph P. Jr., Intramyocardial Pressure: Effect of Preload on Transmural Distribution of Systolic Coronary Blood Flow, The American Journal of Cardiology, vol. 35 (Jun. 1975), pp. 904–911.

Burch, et al., An International Publication for the Study of the Circulation, American Heart Jounal, (Jan. 1980), pp. 8–9.

Lee et al., Effects of laser irradiation delivered by flexible fiberoptic system on the left ventricular internal myocardium, AMJ, (Sep. 1983), vol. 106, No. 3, pp. 587–590.

Galioto, et al., Right coronary artery to left ventricle fistula, AHJ, vol. 82, No. 1, (Jul. 1971), No. 1, p. 93–97.

Levinsky, et al., The Revival of the Horseshoe Graft, The Thoracic and Cardiovascular Surgeon, vol. 27, No. 5, (Oct. 1979), pp. 281–344.

Medical Industry Today Headline News, Device and Diagnostics, (Jul. 17, 1998), Article #07179802, Article is 349 words long, pp. 1–2.

Medical Industry Today Headline News, Financial News, (Jul. 17, 1998), Article 07179808; article is 560 words long, pp. 1–2.

Munro, et al., The possibility of myocardial revascularization by creation of a left ventriculocoronary artery fistula, The Journal of Thoracic and Cardiovascular Surgery, vol. 58, (1969), pp. 25–32.

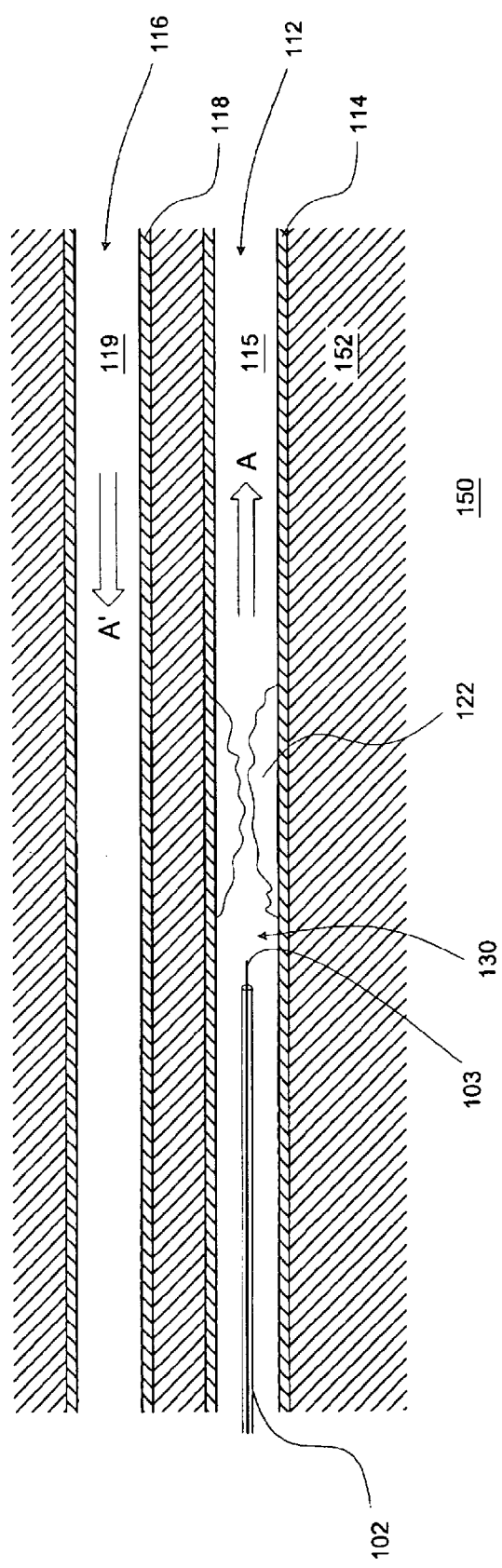

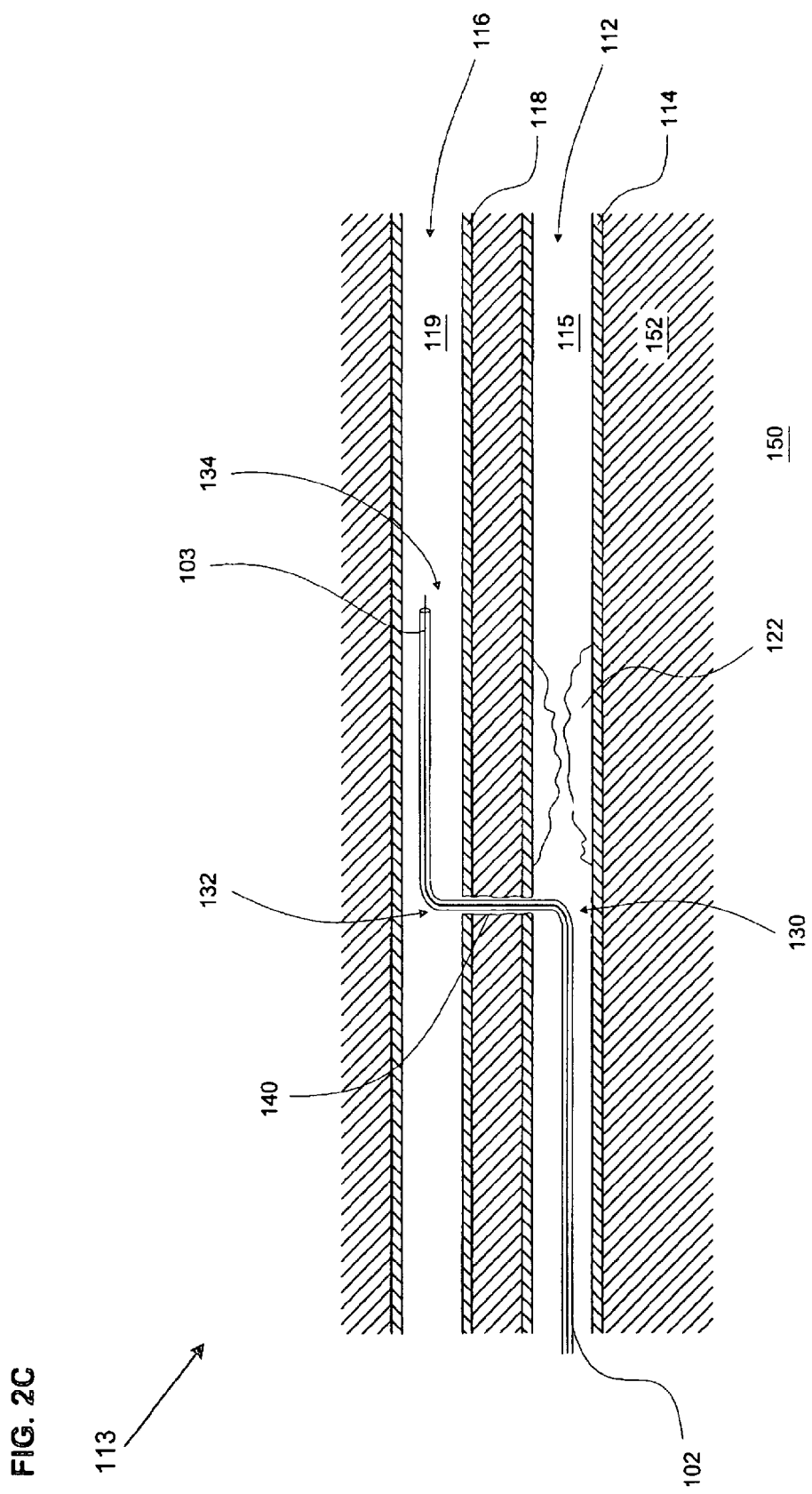

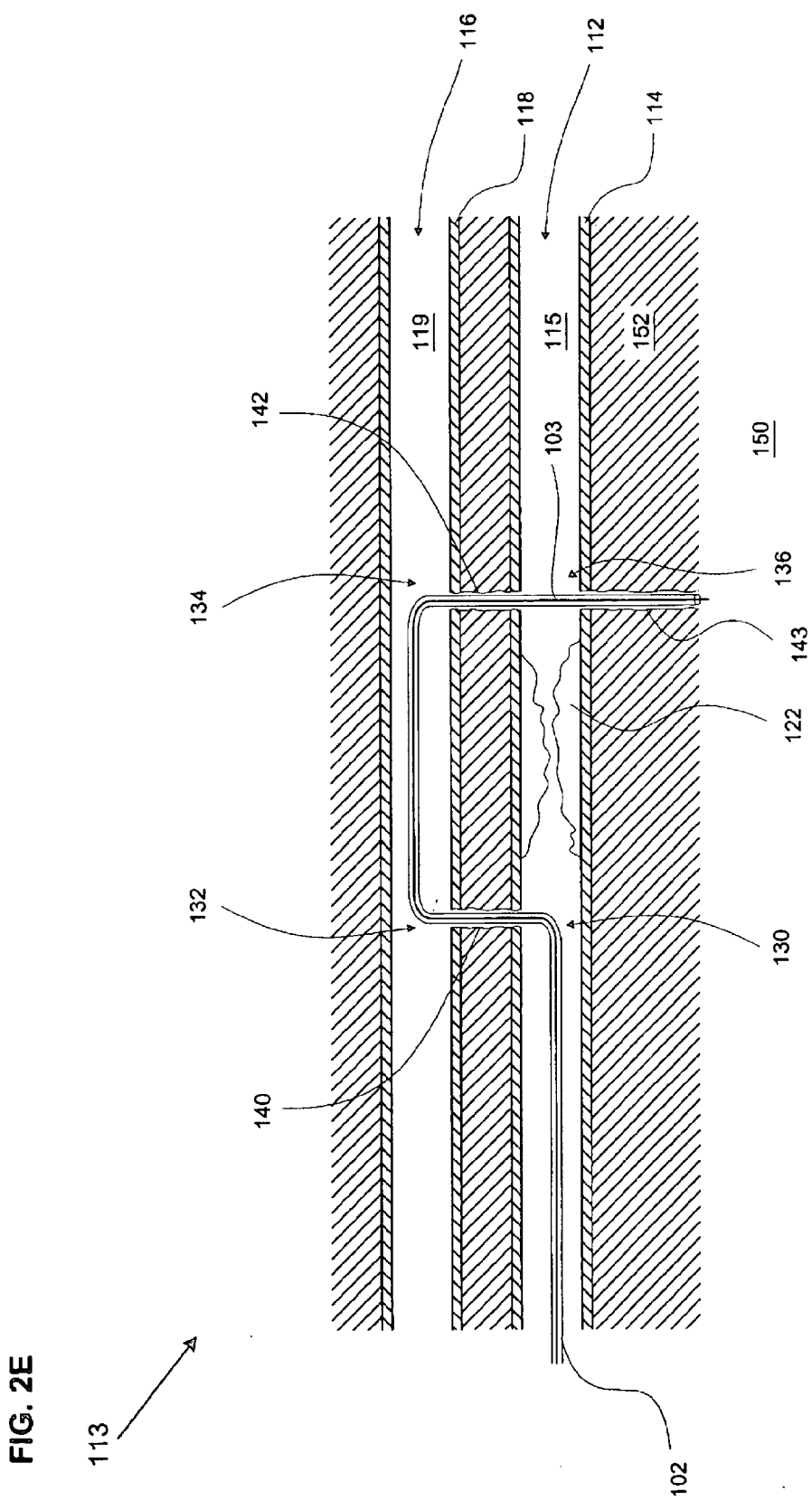

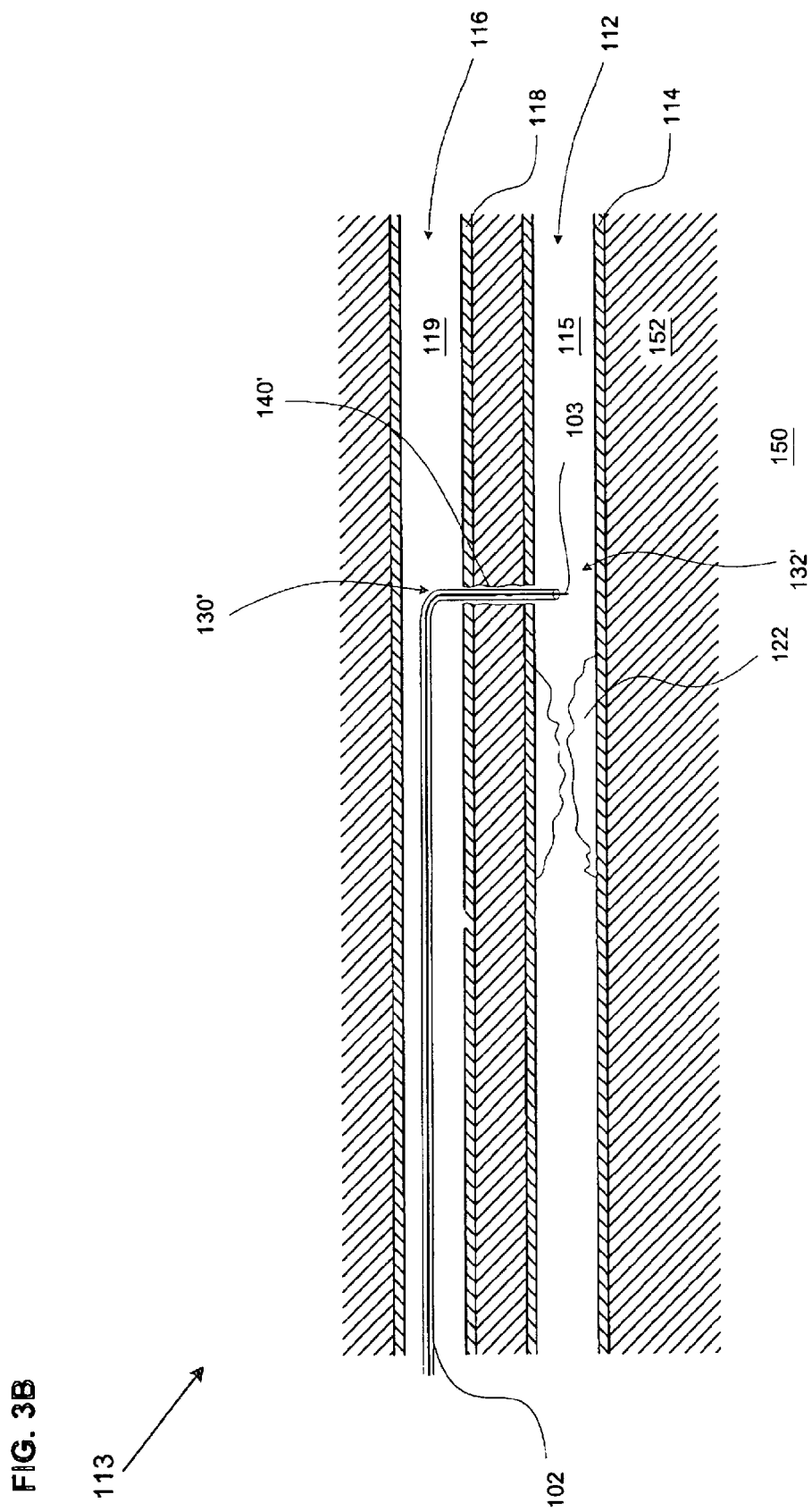

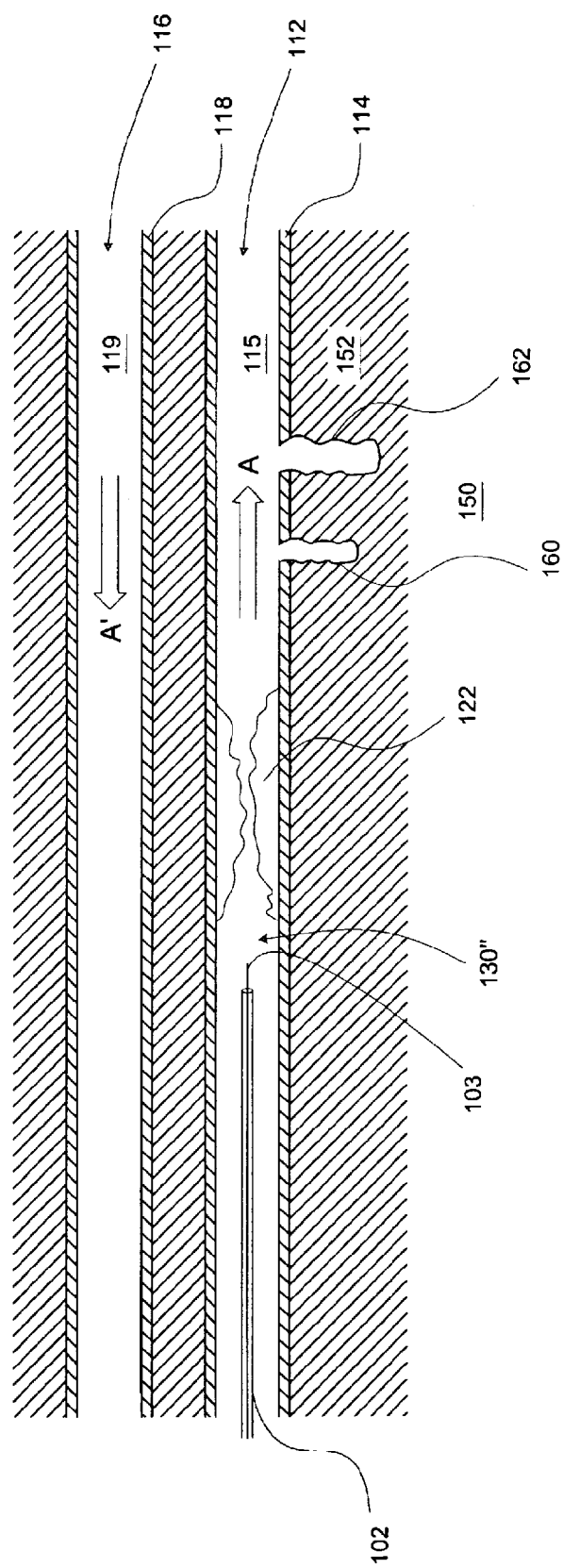

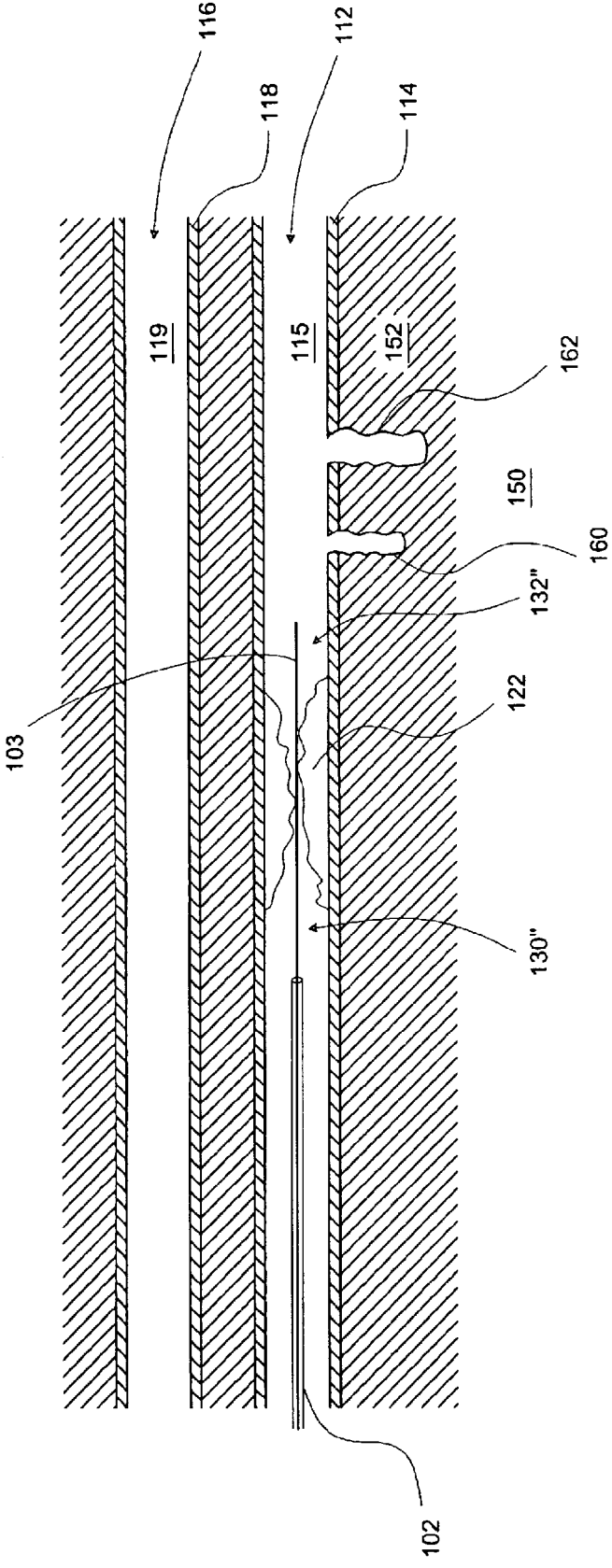

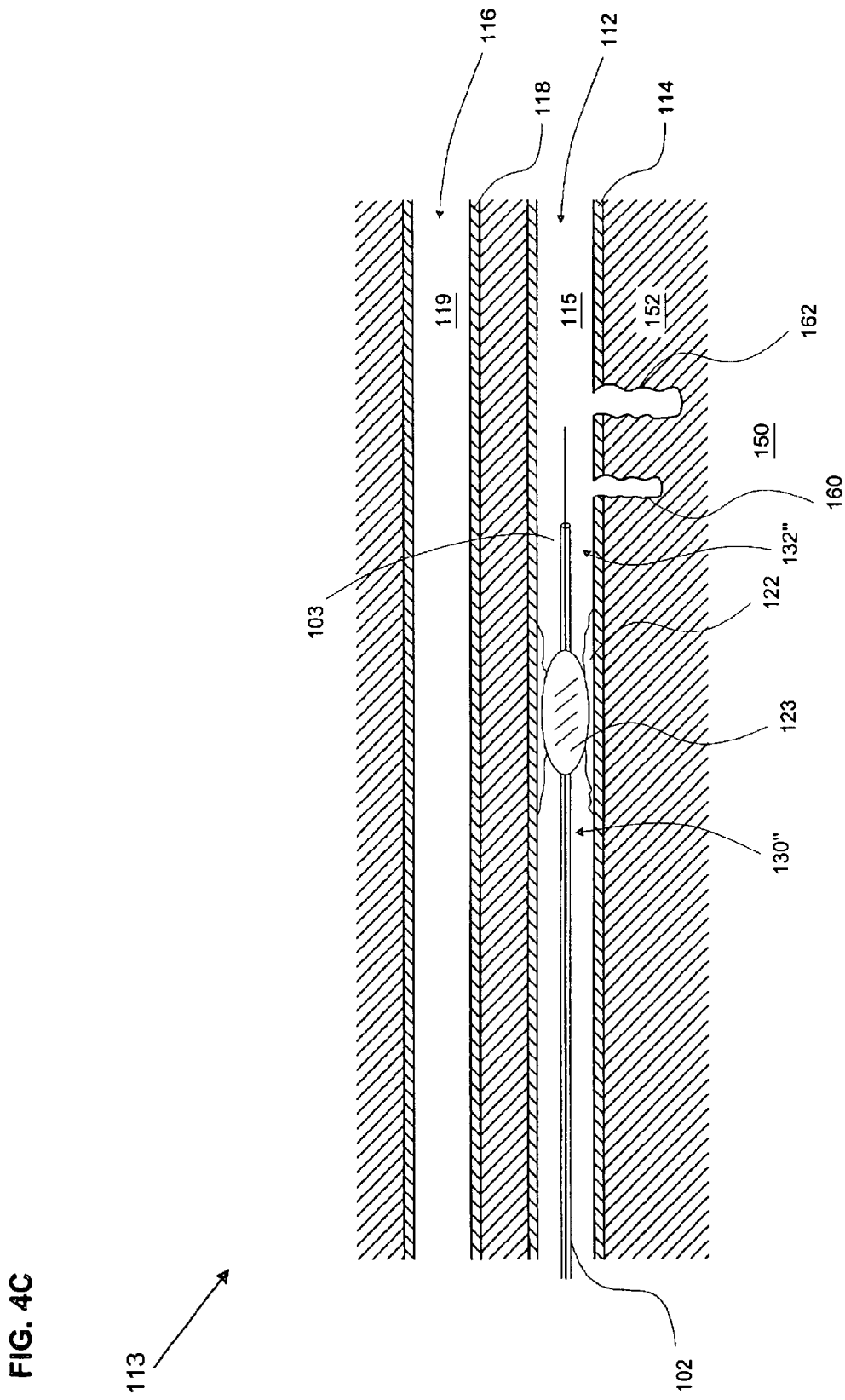

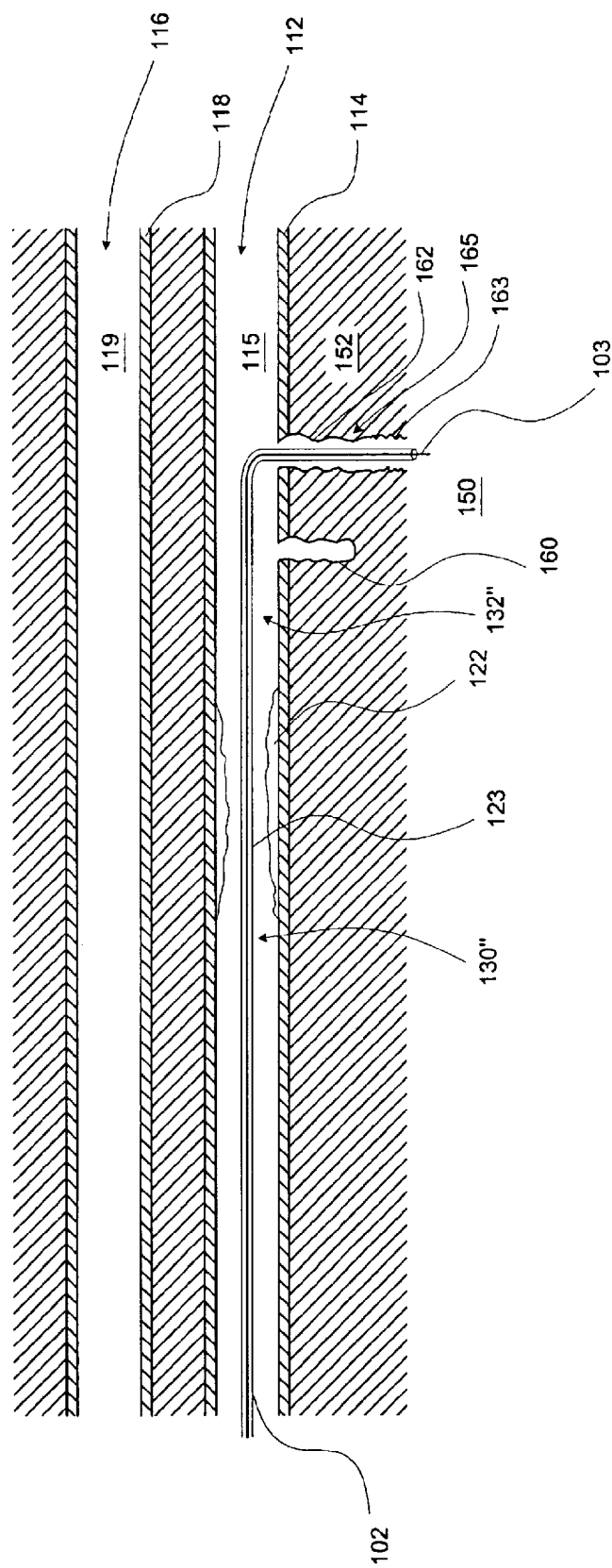

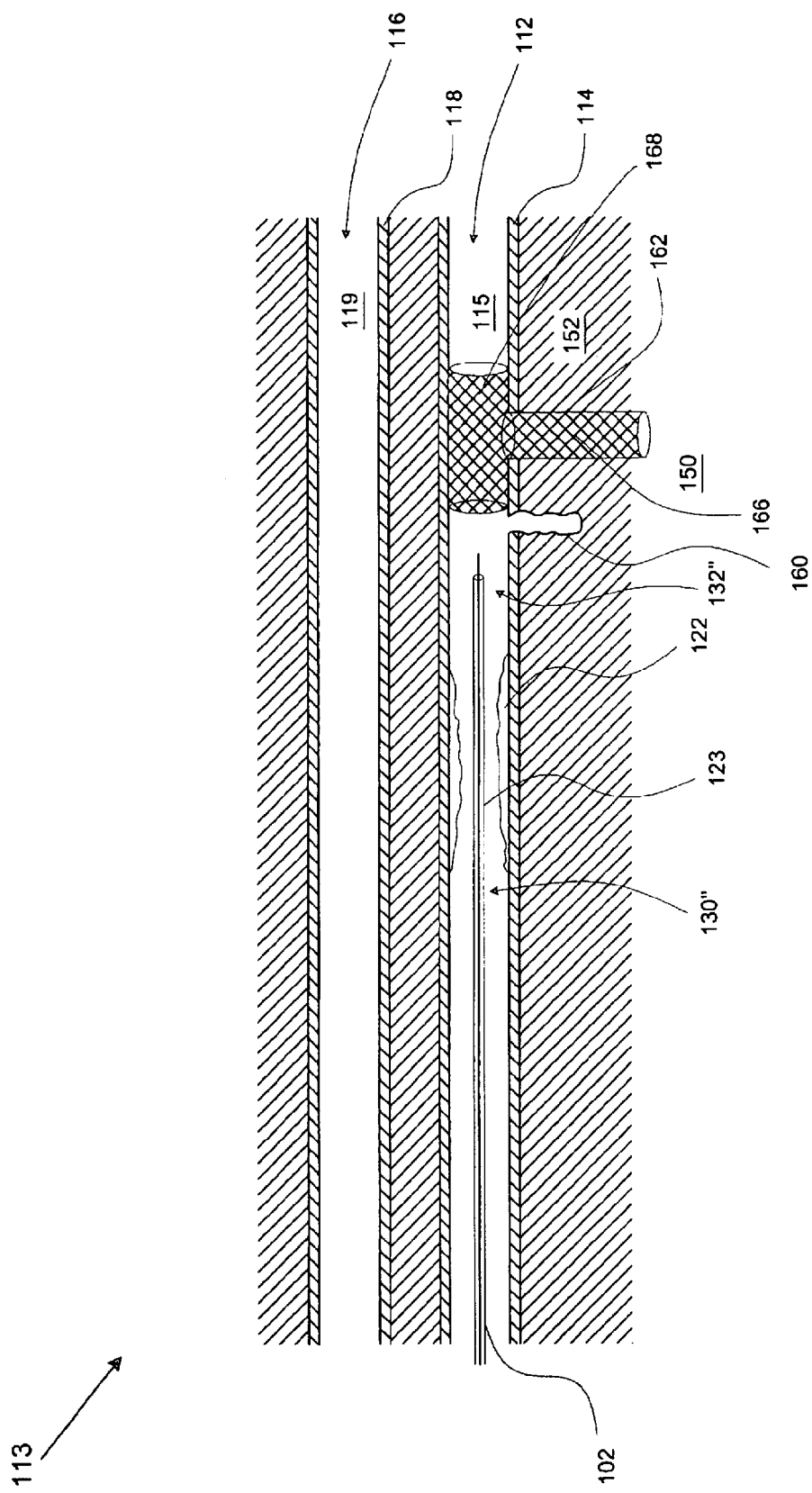

INTRAVASCULAR VENTRICULOCORONARY BYPASS VIA A SEPTAL PASSAGEWAY

TECHNICAL FIELD

The present invention relates generally to a method for performing a coronary artery bypass procedure and, more particularly, to a method for performing an intravascular coronary artery bypass procedure providing a direct flow path from a heart chamber to the coronary artery.

BACKGROUND

Coronary artery disease (e.g., the accumulation of arteriosclerotic plaque within a coronary artery) is the leading cause of premature death in industrialized societies. Modern medical science has developed several procedures for treating coronary artery disease. For example, one method for treating coronary artery disease involves harvesting a saphenous vein or other venous or arterial conduit from elsewhere in the body, or using an artificial conduit, such as one made of expanded polytetrafluoroethylene (ePTFE) tubing, and connecting this conduit as a bypass graft from a viable artery or a chamber of the heart to the coronary artery downstream of the blockage or narrowing. While such treatments are well-established medical procedures, they are not without shortcomings. For example, the number of bypass conduits available for harvesting from the patient is limited. Furthermore, these procedures typically cause significant tissue damage to the patient at the harvest site as well as at the patient's chest.

In addition to the bypass procedures mentioned above, several intravascular methods exist that allow surgeons to re-open the diseased artery, such as, angioplasty or atherectomy. Angioplasty involves the intravascular introduction of a balloon-equipped catheter into the diseased blood vessel. Once the catheter is guided to the appropriate location, the balloon is inflated compressing the arteriosclerotic plaque against the wall of the blood vessel. Atherectomy results in the physical desolution of plaque within the diseased blood vessel using a catheter equipped with a removal tool (e.g., a cutting blade or high-speed rotating tip). While these procedures are less-invasive and are effective in treating the diseased blood vessel, there are shortcomings with these procedures. For example, many existing intravascular procedures do not allow the surgeon to bypass the obstruction. Instead, separate catheter devices are typically inserted in the patient to achieve, for example, revascularization of the blood vessel at a location downstream from the obstruction.

Improvements in intravascular procedures used for treating coronary artery disease are, therefore, sought.

SUMMARY

The present invention relates generally to a method for performing a coronary artery bypass procedure. More particularly, the present invention relates to a method for performing an intravascular coronary artery bypass procedure providing a direct flow path from a heart chamber to the coronary artery. The method of the present disclosure is preferably utilized where the patient's vascular system is used as a conduit for accessing or reaching a desired location within the patient's body.

In one aspect of the disclosure, a method for supplementing a flow of blood to a portion of the cardiovascular system of a patient is disclosed. The method can comprise inserting a catheter device into the vasculature of the patient and advancing the catheter device to a first location within a first coronary vessel within the cardiovascular system; guiding the catheter device through an interstitial passageway formed between the first location and a second location within a second coronary vessel that is distal to an obstruction in the second coronary vessel; forming a blood flow path from a heart chamber directly to the second coronary vessel; and occluding the interstitial passageway between the first coronary vessel and the second coronary vessel to prevent blood flow through the interstitial passageway. In this aspect, the second coronary vessel is a coronary artery, such as, the left anterior descending coronary artery. Similarly, the first coronary vessel is a coronary vein proximate to the coronary artery, such as, the great cardiac vein.

Further to this aspect, forming a blood flow path from the heart chamber directly to the second coronary vessel can include placing a conduit in a heart wall between the heart chamber and the second coronary vessel. Moreover, placing a conduit in a heart wall between the heart chamber and the second coronary vessel can include placing a conduit in a septal passageway extending into the heart wall between the heart chamber and the second coronary vessel.

Still further in this aspect, the interstitial passageway is formed through a wall of the first coronary vessel and through a wall of the second coronary vessel between the first and second locations. In so doing, occluding the interstitial passageway can include deploying an embolization substance at the wall of the first vessel and at the wall of the second vessel. Alternatively, occluding the interstitial passageway includes deploying an embolization device within the interstitial passageway.

In another aspect of the invention, the method can comprise inserting a catheter device into the vasculature of the patient and advancing the catheter device to a first location within a first coronary vessel within the cardiovascular system; guiding the catheter device through a first interstitial passageway formed between the first location and a second location within a second coronary vessel within the cardiovascular system; advancing the catheter device to a third location within the second coronary vessel; guiding the catheter device through a second interstitial passageway formed between the third location and a fourth location within the first coronary vessel that is distal to an obstruction in the first coronary vessel; forming a blood flow path from a heart chamber directly to the first coronary vessel; and occluding the first and second interstitial passageways between the first coronary vessel and the second coronary vessel to prevent blood flow through either of the first or second passageways. In this aspect, the first coronary vessel is a coronary artery, such as, the left anterior descending coronary artery. Similarly, the second coronary vessel is a coronary vein proximate to the coronary artery, such as, the great cardiac vein.

Further to this aspect, forming a blood flow path from the heart chamber directly to the first coronary vessel can include placing a conduit in a heart wall between the heart chamber and the first coronary vessel. Moreover, placing a conduit in a heart wall between the heart chamber and the first coronary vessel can include placing a conduit in a septal passageway extending into the heart wall between the heart chamber and the first coronary vessel.

Still further in this aspect, the first interstitial passageway is formed through a wall of the first coronary vessel and through a wall of the second coronary vessel between the first and second locations. Likewise, the second interstitial passageway is formed through a wall of the second coronary vessel and through a wall of the first coronary vessel between the third and fourth locations. In so doing, occluding the first and second interstitial passageways can include deploying an embolization substance at the wall of the first coronary vessel and at the wall of the second coronary vessel at the first interstitial passageway; and deploying an embolization substance at the wall of the first coronary vessel and at the wall of the second coronary vessel at the second interstitial passageway. Alternatively, occluding the first and second interstitial passageways can include deploying an embolization device within each of the first and second passageways.

In still another aspect of the invention, the method can comprise inserting a catheter device into the vasculature of the patient and advancing the catheter device to a first location within a coronary vessel within the cardiovascular system that is proximate to an obstruction within the coronary vessel; advancing the catheter device through the obstruction to a second position distal to the obstruction; guiding the catheter device through an interstitial passageway extending into a heart wall between a heart chamber and the coronary vessel; and placing a conduit in the interstitial passageway extending into the heart wall between the heart chamber and the coronary vessel. In this aspect, the coronary vessel can be a coronary artery.

Further in this aspect, the method can further comprise distending the obstruction within the coronary vessel. Accordingly, distending the obstruction within the coronary vessel can include inflating a balloon at the obstruction within the coronary vessel. Moreover, the interstitial passageway can include a septal passageway extending into the heart wall between the heart chamber and the coronary vessel.

BRIEF DESCRIPTION OF THE DRAWINGS

The invention may be more completely understood in consideration of the following detailed description of various embodiments of the invention in connection with the accompanying drawings, in which:

FIGS. 2A–2G depict one possible embodiment of the method for performing an intravascular coronary artery bypass procedure in accordance with the principles of the present disclosure;

FIGS. 3A–3E depict a second possible embodiment of the method for performing an intravascular coronary artery bypass procedure in accordance with the principles of the present disclosure; and FIGS. 4A–4E depict a third possible embodiment of the method for performing an intravascular coronary artery bypass procedure in accordance with the principles of the present disclosure;

Figure 1:
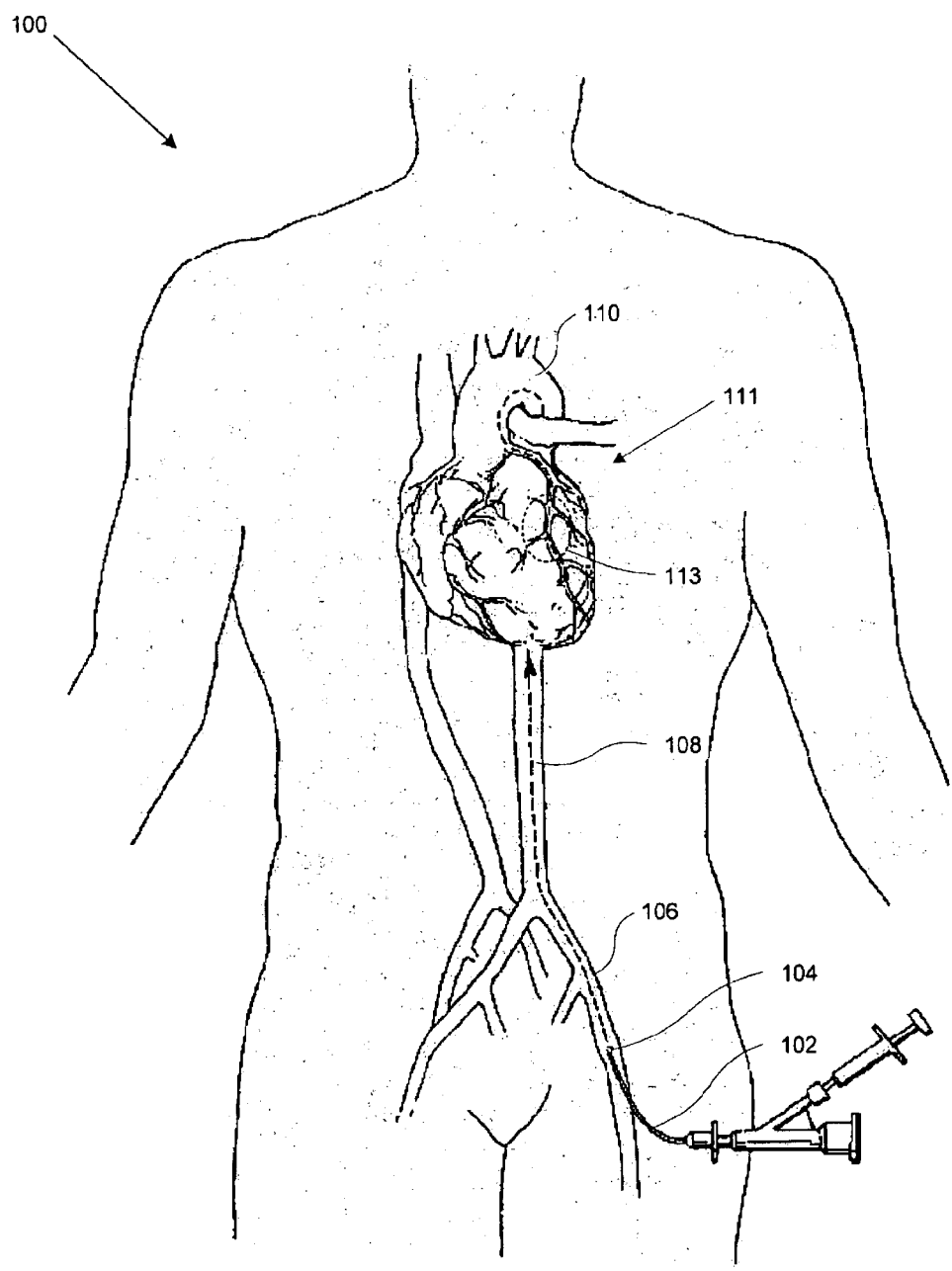
FIG. 1 is a high-level schematic illustration of an intravascular catheter being advanced throughout a patient's vascular system in accordance with the principles of the present disclosure.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

Various embodiments of the present invention will be described in detail with reference to the drawings, wherein like reference numerals represent like parts and assemblies throughout the several views. Reference to various embodiments does not limit the scope of the present invention, which is limited only by the scope of the claims attached hereto.

The following discussion is intended to provide a brief, general description of a method of intravascular treatment of a diseased blood vessel within a patient's vascular system. The method of the present disclosure may be implemented during any intravascular surgical procedure where it is desirous to utilize the patient's vascular system as a conduit for accessing or reaching a desired location within the patient's body to effect an appropriate medical intervention.

As will become apparent from the discussion below in connection with the accompanying drawings, the present disclosure has particularized applicability to the treatment of diseased blood vessels within the patient's cardiovascular system. However, it will be appreciated by those having skill in the art that the present disclosure is not limited to the specific embodiments discussed below. Rather, the present disclosure has general applicability to situations where it is desirable to treat a diseased blood vessel by utilizing the patient's vascular system as a conduit for accessing or reaching a desired location within the patient's body.

Moreover, in the most preferred embodiments, the left ventricle is the chamber of the heart utilized. There are two reasons for this selection. First, the left ventricle normally provides blood to the coronary arteries, because it pumps blood into the aorta from which the coronary arteries branch. Therefore, the magnitude of the blood pressure peak generated by the left ventricle is most similar to the blood pressure peak the proximal coronary artery would normally experience. Second, the blood which flows into the left ventricle is returning from the lungs. In the lungs, the blood acquires oxygen and loses carbon dioxide. Thus, the blood available by shunting from the chambers of the left side of the heart will have a higher oxygen and lower carbon dioxide content than blood within the right-side chambers.

Now referring to FIG. 1, an exemplary intravascular coronary artery bypass procedure will be described. As described above, such procedures allow surgeons to effectively treat a diseased blood vessel with minimal invasiveness to the patient 100 being treated. The phrase "diseased blood vessel" is generally meant to include any blood vessel having a diminished blood flow capacity due to, for example, a build-up or accumulation of arteriosclerotic plaque within the vessel. Moreover, because these procedures are performed using catheters that are introduced remotely, normal tissue injury associated with other procedures can be minimized.

As shown in FIG. 1, an intracoronary catheter device 102 is inserted into a patient 100 via an incision. In the illustrated embodiment, the catheter device 102 can be a guide catheter capable of atraumatically advancing through the patient's 100 arterial system. Alternatively, as is commonly understood in the art, the catheter device 102 can include (or used in conjunction with) any catheter device capable of effecting a desired medical or therapeutic intervention. For example, the catheter device 102 can be equipped with (or used in conjunction with separate catheters that are equipped with) ablation devices, endoscopic devices, surgical tools, such as, needles, cannula, catheter scissors, graspers, or biopsy devices, and energy delivery devices, such as, laser fibers, bipolar and monopolar radio frequency ("RF") conductors, microwave antennae, radiation delivery devices, and thermal delivery devices.

As shown in FIG. 1, the catheter 102 can be inserted via an incision located at or near the groin 104 and advanced through the patient's 100 arterial system towards the diseased blood vessel. While many paths through the patient's 100 arterial system are contemplated, as shown in the embodiment illustrated in FIG. 1, the catheter 102 can be advanced towards the diseased blood vessel within the patient's cardiovascular 111 system via the femoral artery 106. Through continued advancement within the descending aorta 108 and the ascending aorta 110, the patient's 100 cardiovascular system 111 is entered. The catheter 102 is advanced through the cardiovascular system 111 until it is positioned within the diseased coronary blood vessel proximate to the treatment zone or diseased portion 113 of the cardiovascular system 111.

As discussed above, the present disclosure provides a method for utilizing the patient's 100 vascular system as a conduit for accessing or reaching to a desired location with the patient's 100 body. The desired location within the patient's 100 vascular system can be determined through standard radiographic techniques well-known to those having ordinary skill in the art. Once at the desired location (e.g., the treatment zone or diseased portion 113), a surgeon can treat the diseased coronary blood vessel by revascularizing the diseased blood vessel. In particular, the method of the present disclosure provides for the transmycardial revascularization of the diseased blood vessel by establishing a channel leading from a chamber of the patient's 100 heart into the diseased blood vessel. This will be described in greater detail below.

Figure 2B:
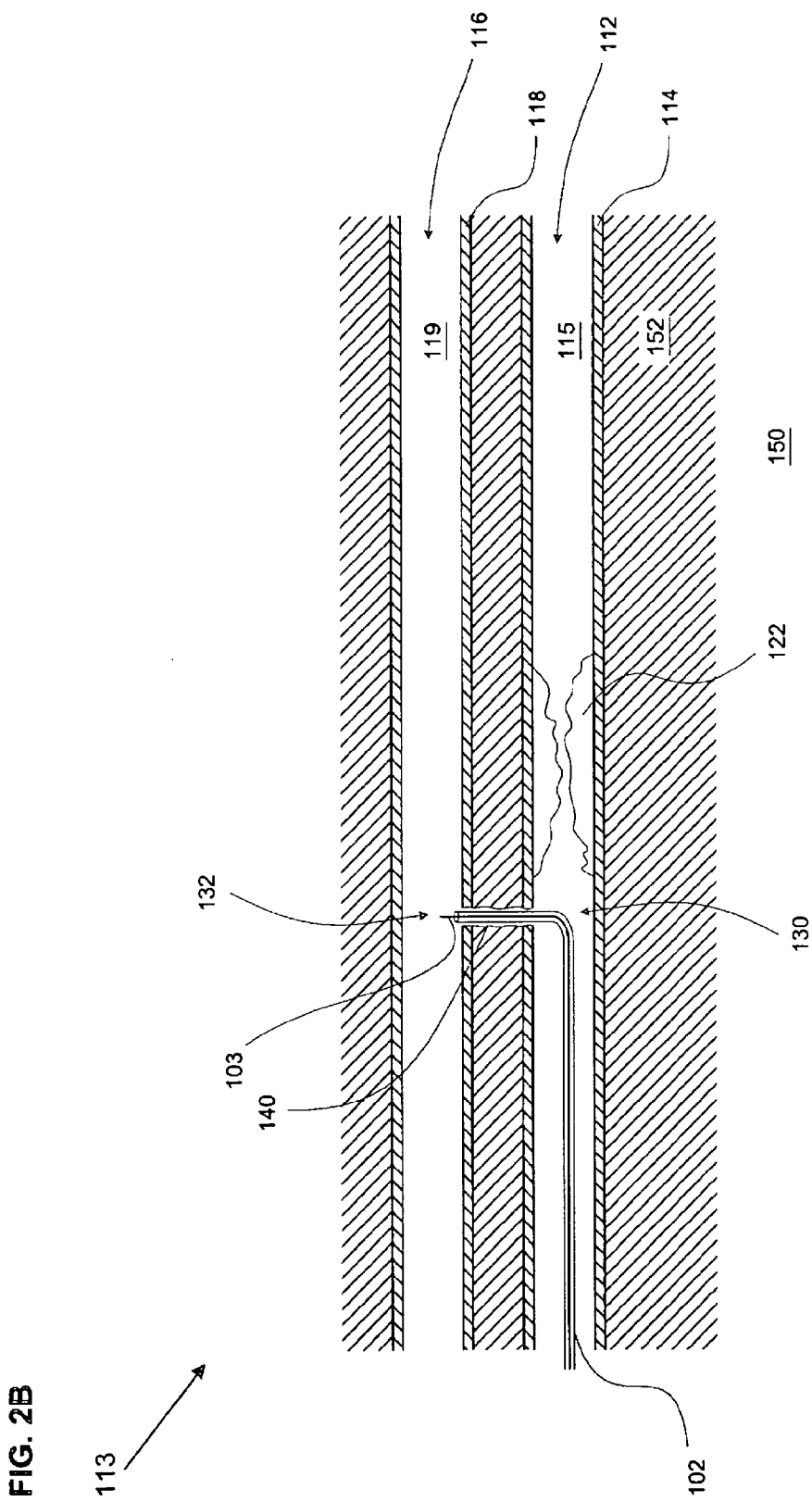

Now referring to FIGS. 2A–2G, the catheter device 102 is advanced through the patient's 100 (FIG. 1) arterial system into the cardiovascular system 111 (FIG. 1). As is commonly understood, the catheter device 102 can be guided through the patient's 100 vascular system over a guide wire 103. The guide wire 103 permits the atraumatic advancement of the catheter 102 and/or additional instrumentation (e.g., ablation devices, etc.) into the diseased coronary vessel. As shown in FIG. 2A, the catheter device 102 is advanced into the cardiovascular system 111 and positioned within a first coronary blood vessel 112. In the illustrated embodiment, the first blood vessel 112 is a diseased coronary blood vessel, such as, a diseased coronary artery. More particularly, the first blood vessel 112 can be the Left Anterior Descending coronary artery. As is commonly understood, the first blood vessel 112 (e.g., the coronary artery) proceeds along the surface of the heart proximate to or adjacent to a second coronary blood vessel 116. In the illustrated embodiment, the second coronary blood vessel 116 is a coronary vein, such as, the Great Cardiac Vein. Due to the arrangement and/or proximity of the first blood vessel 112 (e.g., the coronary artery) with respect to the second blood vessel 116 (e.g., the coronary vein), either of two can be used as a conduit for accessing or reaching a desired location within the other.

The wall 114 of the first blood vessel 112 (e.g., the coronary artery) defines a lumen 115 that serves to deliver oxygenated blood to the patient's 100 heart muscle (e.g., the myocardium 152). The blood flow through the first blood vessel 112 flows in the direction of arrow A. Moreover, as shown throughout FIGS. 2A–2G, arteriosclerotic plaque has accumulated at the treatment zone 113 to form an obstruction 122. The obstruction 122 acts to reduce the volume of blood flow through the first blood vessel 112 (e.g., the coronary artery) along the direction of arrow A. Similarly, the wall 118 of the second blood vessel 116 (e.g., the coronary vein) defines a lumen 119 that serves to return oxygen depleted blood to the right atrium. The blood flow through the second blood vessel 116 flows in the direction of arrow A'. While the illustrated embodiments show the first and second blood vessels 112, 116 being separated, it should be understood that this is for illustrative purposes and that such a separation may not exist. Instead, for example, the wall 114 of the first coronary blood vessel 112 may be immediately adjacent to or in contact with the wall 118 of the second coronary blood vessel 116.

In accordance with the method of the present disclosure, the catheter device 102 can be advanced within the patient's 100 vascular system to a first location 130 within the first blood vessel 112 (e.g., the coronary artery). In the illustrated embodiment, the first location 130 is situated proximate to the obstruction 122. As discussed above, it is often desirous to treat the diseased blood vessel (e.g., via revascularization or any other suitable technique or medical intervention) by situating the catheter 102 downstream or distal to the obstruction 122. In one possible embodiment, this can be accomplished by diverting the catheter 102 around the obstruction 122. In particular, as will be discussed in connection with FIGS. 2B–2G, the catheter 102 can be diverted from within the first blood vessel 112 into the second blood vessel 116, thereby, allowing the catheter 102 to be advanced to a location distal to the obstruction 122 without advancing through the obstruction 122. However, one skilled in the art will readily appreciate that the catheter 102 can be situated downstream or distal to the obstruction 122 by advancing the catheter 102 through the obstruction 122 (as will be described in connection with FIGS. 4A–4E).

In one possible embodiment, the catheter 102 can be guided to a location distal to the obstruction 122 by being diverted from within the first coronary vessel 112 (e.g., the coronary artery) into the second coronary blood vessel 116 (e.g., the coronary vein). To accomplish this, as shown in FIG. 2B, the catheter device 102 can be equipped with (or used in conjunction with a catheter equipped with) an ablation device, for example, an ablation tip (not shown) capable of ablating or otherwise creating a first interstitial passageway or channel 140 between the first coronary vessel 112 and the second coronary vessel 116. Ablation devices are well-known in the art and typically operate using any suitable power source, such as, laser, radio frequency, or any other similar power source. Moreover, as is commonly understood in the art, power to the ablating tip (not shown) can be synchronized such that the ablation occurs at a recurring aspect of the cardiac cycle. The first interstitial passageway 140 provides a path of communication between the first coronary vessel 112 and the second coronary vessel 116. In one possible embodiment, the first interstitial passageway 140 is formed through the wall 114 of the first coronary vessel 112 and through the wall 118 of the second coronary vessel 116 between the first location 130 and a second location 132 within the second coronary vessel 116. Once the first interstitial passageway 140 has been formed, the catheter device 102 can be guided over the guide wire 103 into the second coronary vessel 116.

Once the catheter device 102 is positioned within the second coronary vessel 116 (e.g., the coronary vein), the catheter 102 can be guided through the lumen 119 as shown in FIG. 2C to a third location 134 within the second coronary vessel 116. In the illustrated embodiment, the third location 134 is situated at a location downstream or distal to the obstruction 122 within the first coronary vessel 112 (e.g., the coronary artery). Once at the third location 134, the catheter 102 can be diverted from within the second coronary blood vessel 116 such that it returns to the first coronary vessel 112.

Figure 2D:
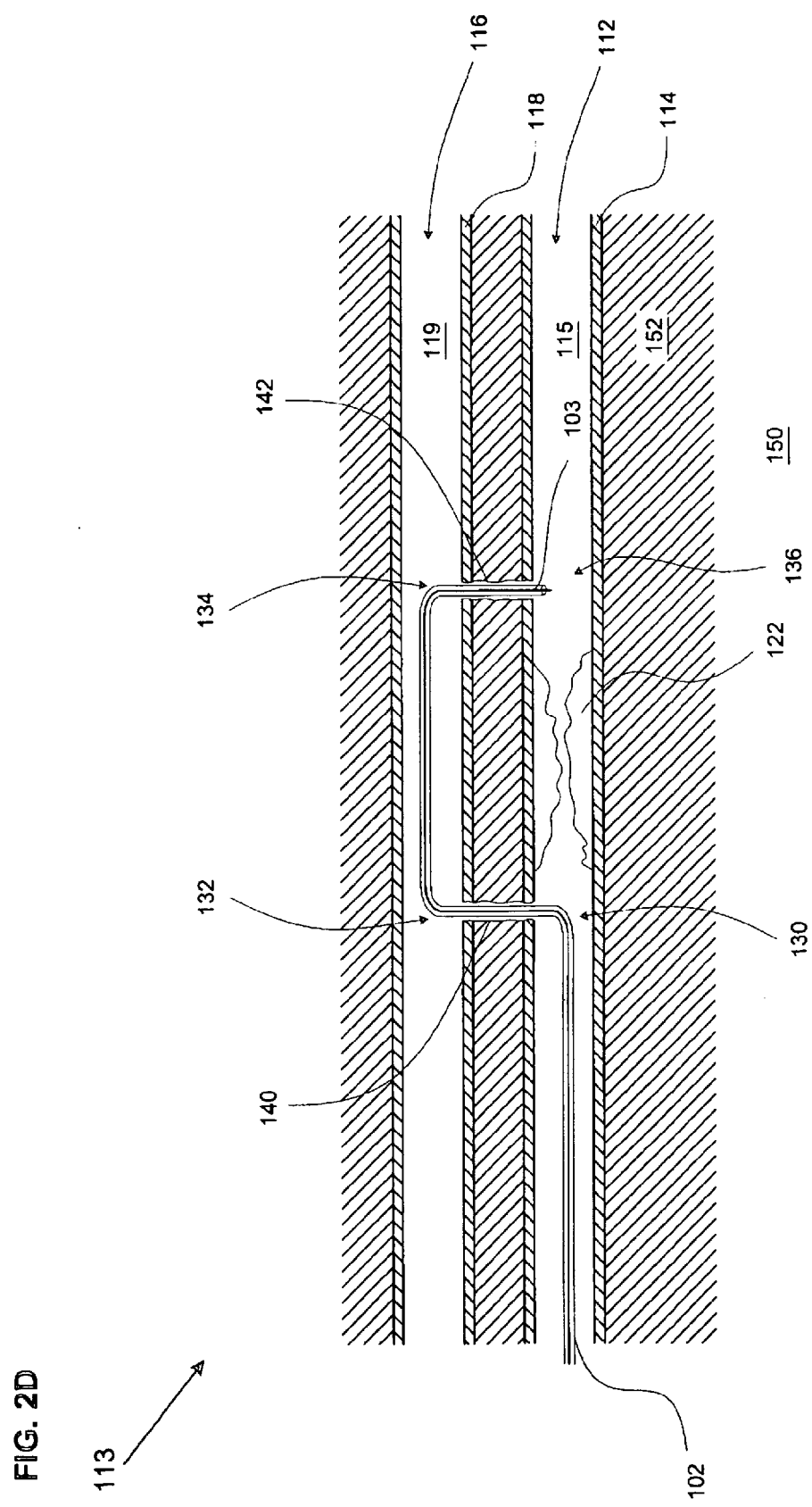
Figure 2F:
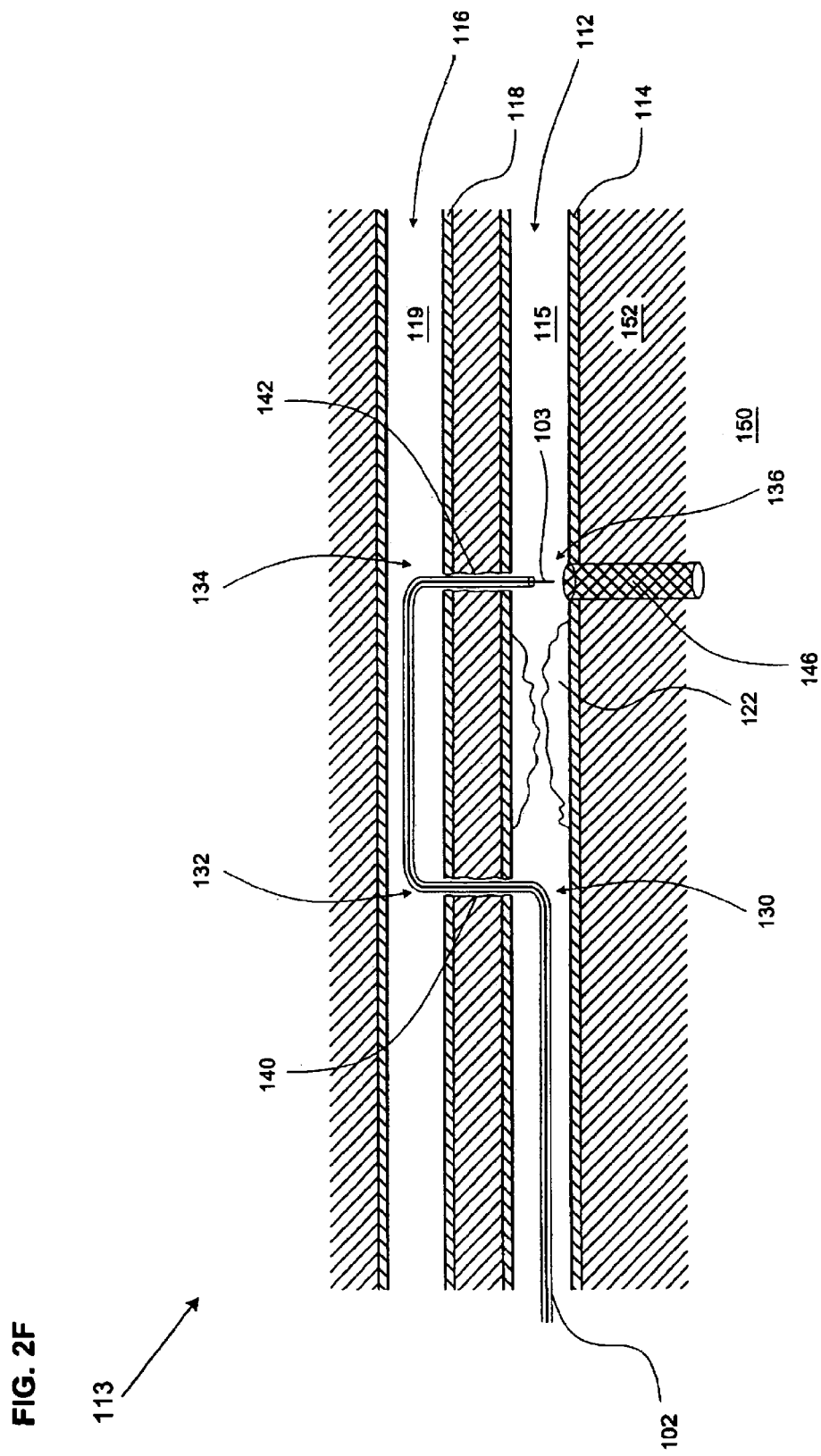
Figure 2G:
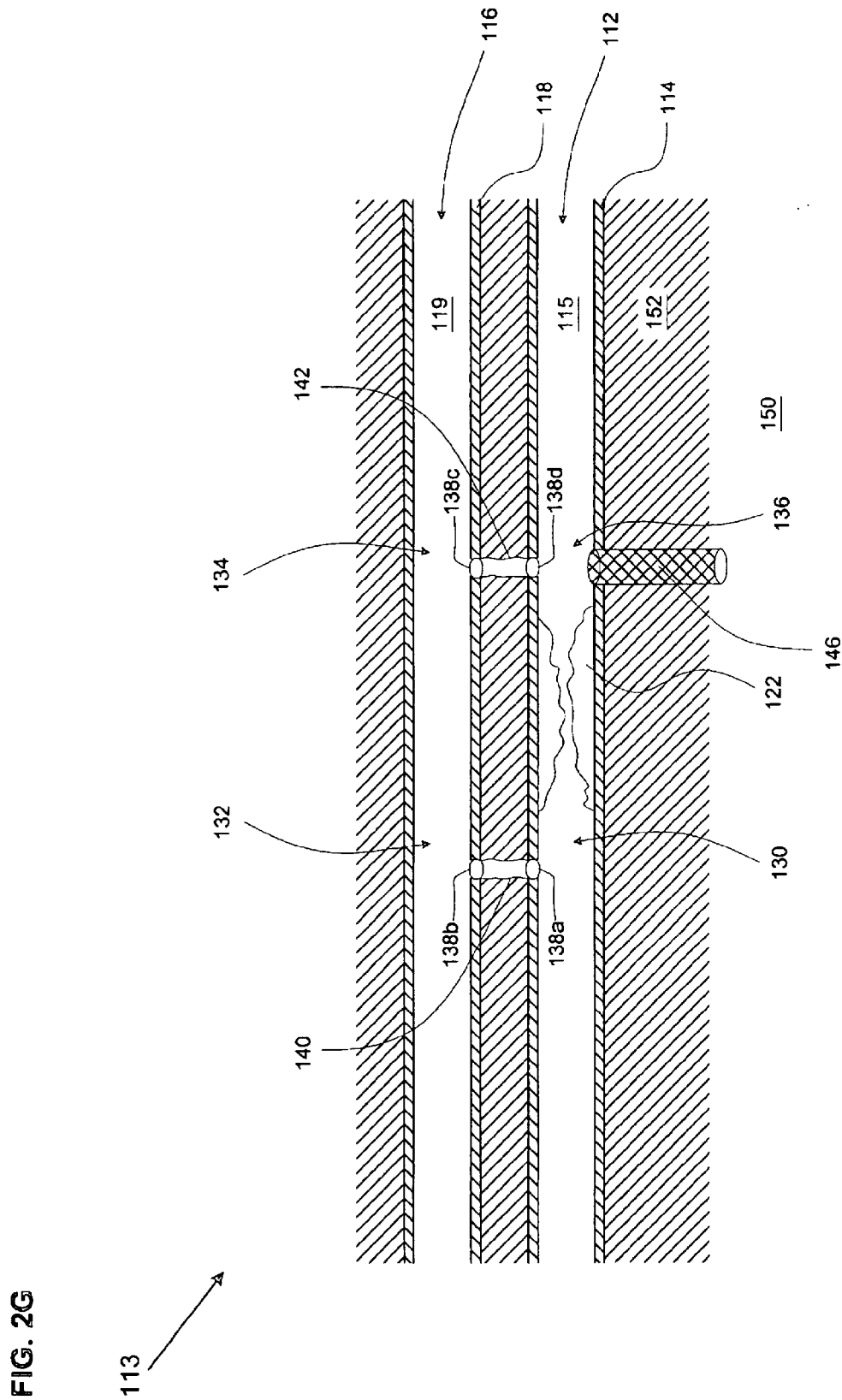

In particular, as shown in FIG. 2D and as discussed above, the catheter device 102 can be equipped with (or used in conjunction with a catheter equipped with) an ablation device, for example, an ablation tip (not shown) capable of ablating or otherwise creating a second interstitial passageway or channel 142 between the second coronary vessel 116 and the first coronary vessel 112. The second interstitial passageway 142 provides a path of communication between the second coronary vessel 116 and the first coronary vessel 112 distal to the obstruction 122. In one possible embodiment, the second interstitial passageway 142 is formed through the wall 118 of the second coronary vessel 116 and through the wall 114 of the first coronary vessel 112 between the third location 134 and a fourth location 136 within the first coronary vessel 112. Once the second interstitial passageway 142 has been formed, the catheter device 102 can be guided over the guide wire 103 into the first coronary vessel 112.

While the first and second interstitial passageways 140, 142 are illustrated as having been created substantially perpendicular to the first and second coronary blood vessels 112, 116, it will be appreciated by those having skill in the art that the first and second interstitial passageways 140, 142 can be formed at any angle suitable for providing a path of communication between the first and second coronary vessels 112, 116, thereby, allowing the catheter device 102 to be diverted into or out of either of the coronary blood vessels 112, 116.

As shown in FIG. 2D, the fourth location 136 is situated downstream or distal to the obstruction 122. Accordingly, the amount of blood flow through the first coronary vessel 112 (e.g., the coronary artery) is reduced due to the obstruction 122. Several methods exist that allow surgeons to treat the diseased blood vessel by supplementing the blood flow through the first coronary vessel 112. In particular, the method of the present disclosure treats the diseased blood vessel by creating a channel that leads directly from a chamber 150 of the heart through the myocardium 152. Various methods and devices for transmyocardial revascularization have been described in U.S. Pat. No. 5,944,019 to Knudson et al., entitled "CLOSED CHEST CORONARY BYPASS," the entire disclosure of which is, hereby, incorporated by reference.

For example, as shown in FIG. 2E, once the catheter 102 is situated at the fourth location 136 within the first coronary vessel 112 (e.g., the coronary artery), a channel 143 can be established between the heart chamber 150 and the first coronary vessel 112. In particular, as shown in FIG. 2E and as discussed above, the catheter device 102 can be equipped with (or used in conjunction with a catheter equipped with) an ablation device, for example, an ablation tip (not shown) capable of ablating or otherwise creating the channel 143 between the first coronary vessel 112 and the heart chamber 150.

Once the channel 143 is formed, a transmyocardial implant 146 (e.g., a conduit) can be deployed within the channel 143. In certain embodiments, the transmyocardial implant 146 can include a tubular reinforcing structure (e.g., a mesh and/or coild tube, a tube defined by a plurality of circumferential and axial struts/supports, etc.) that is expandable from an undeployed state to a deployed state. In the undeployed state, the transmyocardial implant 146 has a reduce diameter sized for allowing the implant to be directed through the patient's 100 vasculature. In the deployed state, the implant has an expanded diameter sized for allowing the transmyocardial implant 146 to be securely held within the channel 143. The reinforcing structure of the transmyocardial implant 146 can be expanded by known techniques (e.g., the structure can be balloon expandable or self expanding). Additionally, some embodiments of the transmyocardial implant 146 can include a liner for preventing thrombosis as shown in U.S. patent application Ser. No. 09/141,284, filed 27 Aug. 1999, the entire disclosure of which is, hereby, incorporated by reference.

During installation, the transmyocardial implant 146 can be positioned within the channel 143 in its undeployed state. Once properly positioned, the transmyocardial implant 146 can be deployed. In it deployed state, the transmyocardial implant 146 is sized to be retained within the formed channel 143. Moreover, once in place, the transmyocardial implant 146 creates a permanent transmyocardial channel between the heart chamber 150 and the coronary artery 112.

In addition to deployment of the transmyocardial implant 146, the first and second interstitial passageways 140, 142 can be blocked or occluded to prevent blood flow through the first and second interstitial passageways 140, 142. In so doing, the method of the present disclosure restores and/or ensures normal coronary aterial and veinous blood flow. To accomplish this, one or more embolization devices can be deployed within each of the first and second interstitial passageways 140, 142. In the embodiment illustrated in FIG. 2G, at least two embolization devices are deployed within each of the first and second interstitial passageways 140, 142. For example, the embolization devices 138a, 138d can be deployed within the first coronary vessel 112 (e.g., the coronary artery) proximate to the wall 114. Similarly, the embolization devices 138b, 138c can deployed within the second coronary vessel 116 (e.g., the coronary vein) proximate to the wall 118. The embolization devices 138a–138d can include any device and/or material capable preventing blood flow through the first and second interstitial passageways 140, 142. For example, the embolization devices 138a–138d can include detachable balloons, coils, strands of coagulation producing material, microfibrillar collagen, collagen sponge, cellulose gel or sponge, such as Gelfoam™, surgical glue, such as, Tissel™ or Genzyme™, special stents, or other similar embolization devices.

An alternative method for treating a diseased blood vessel by utilizing the patient's 100 vascular system as a conduit for accessing or reaching a desired location within the patient's body will now be described in connection with FIGS. 3A–3E. In this embodiment, the catheter device 102 is advanced through the patient's 100 (FIG. 1) arterial system into the cardiovascular system 111 (FIG. 1) and is positioned within the second coronary blood vessel 116 (e.g., the coronary vein). The catheter device 102 can be advanced within the patient's 100 vascular system to a first location 130' within the second coronary blood vessel 116 (e.g., the coronary vein). In the illustrated embodiment, the first location 130' is situated at a location downstream or distal to the obstruction 122 within the first coronary vessel 112 (e.g., the coronary artery).

Once at the first location 130', the catheter 102 can be diverted from within the second coronary blood vessel 116 such that it returns to the first coronary vessel 112. In particular, as shown in FIG. 3B and as discussed above, the catheter device 102 can be equipped with (or used in conjunction with a catheter equipped with) an ablation device, for example, an ablation tip (not shown) capable of ablating or otherwise creating an interstitial passageway or channel 140' between the second coronary vessel 116 and the first coronary vessel 112. The second interstitial passageway 142 provides a path of communication between the second coronary vessel 116 and the first coronary vessel 112 distal to the obstruction 122. In one possible embodiment, the interstitial passageway 140' is formed through the wall 118 of the second coronary vessel 116 and through the wall 114 of the first coronary vessel 112 between the first location 130' and a second location 132' within the first coronary vessel 112. Once the interstitial passageway 142 has been formed, the catheter device 102 can be guided over the guide wire 103 into the first coronary vessel 112.

While the interstitial passageway 140' is illustrated as having been created substantially perpendicular to the first and second coronary blood vessels 112, 116, it will be appreciated by those having skill in the art that the interstitial passageway 140' can be formed at any angle suitable for providing a path of communication between the first and second coronary vessels 112, 116, thereby, allowing the catheter device 102 to be diverted into or out of either of the coronary blood vessels 112, 116.

Figure 3A:
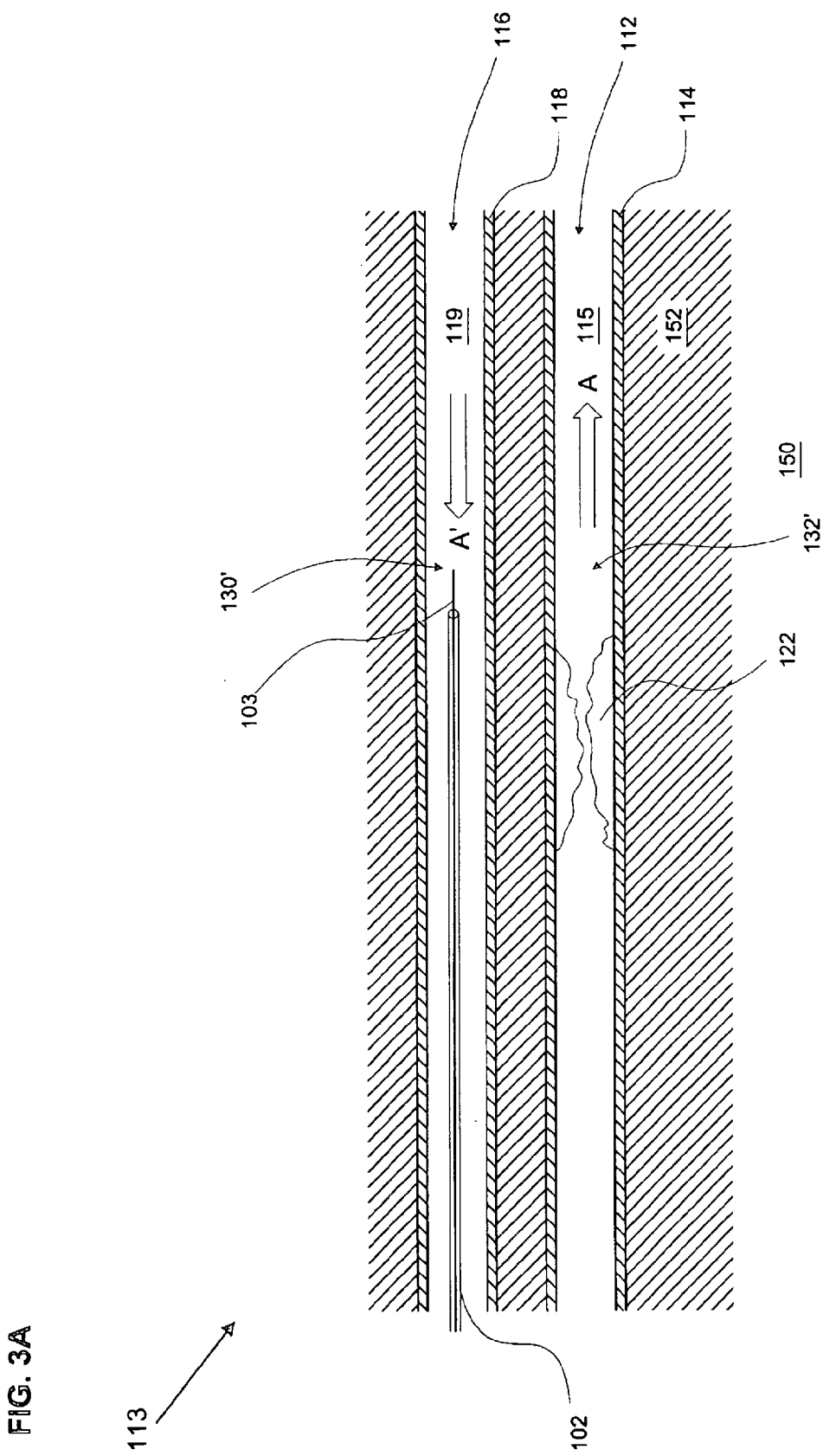
Figure 3C:
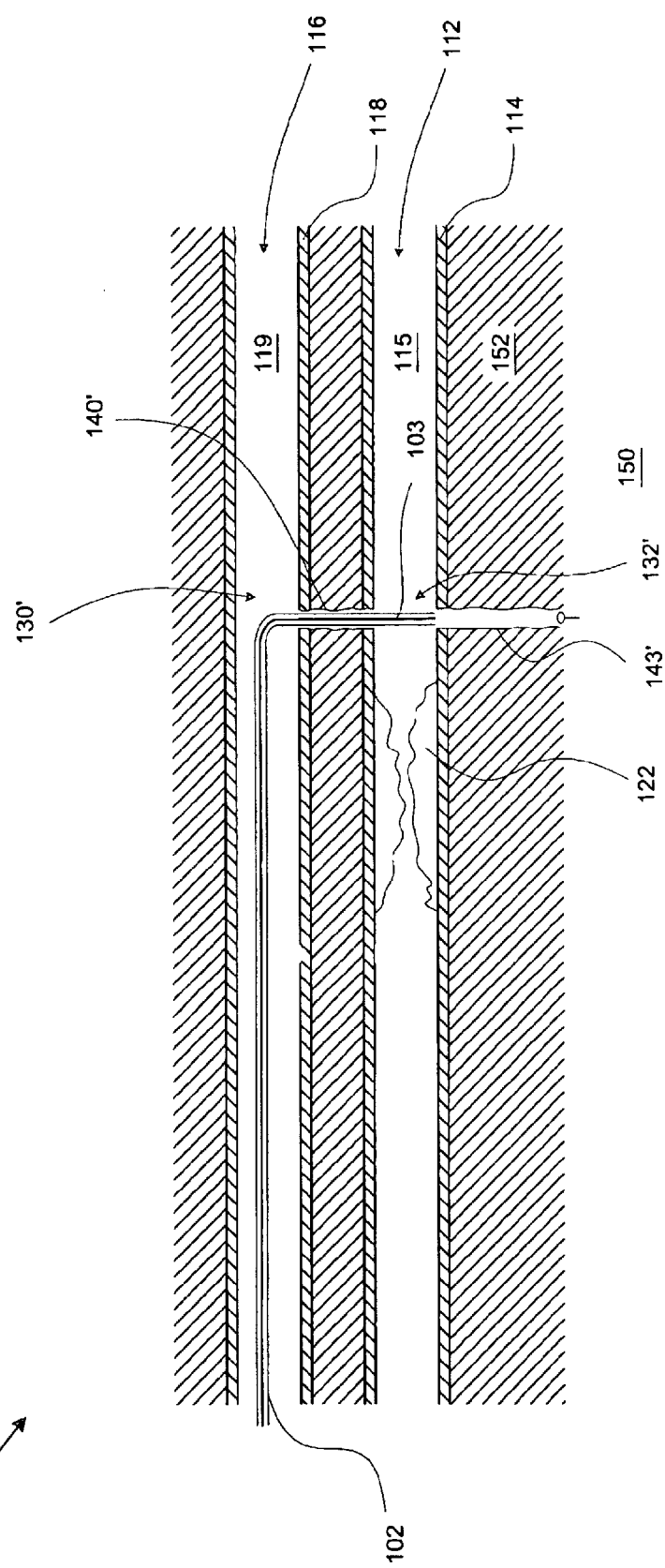
Figure 3D:
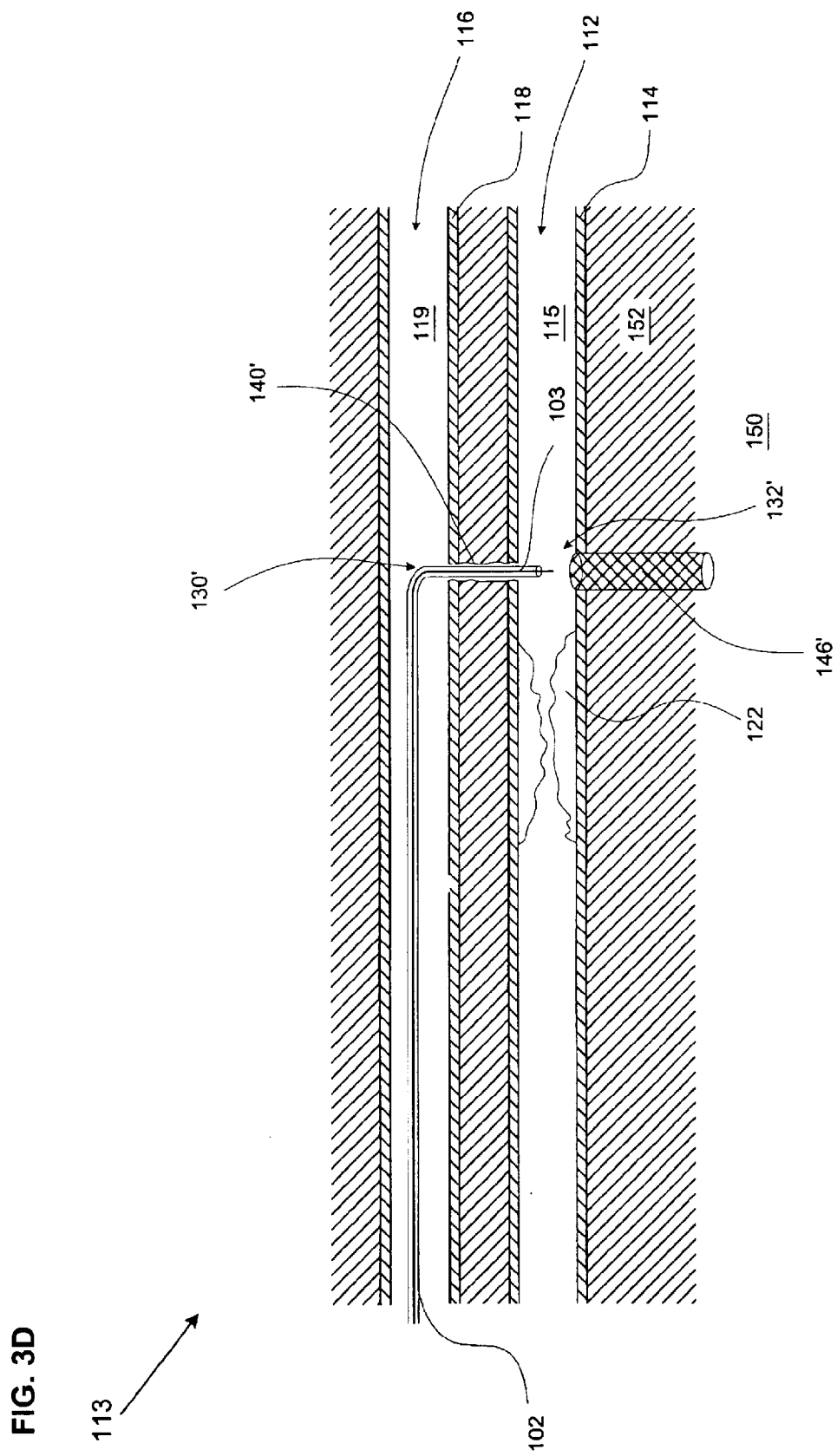
Figure 3E:
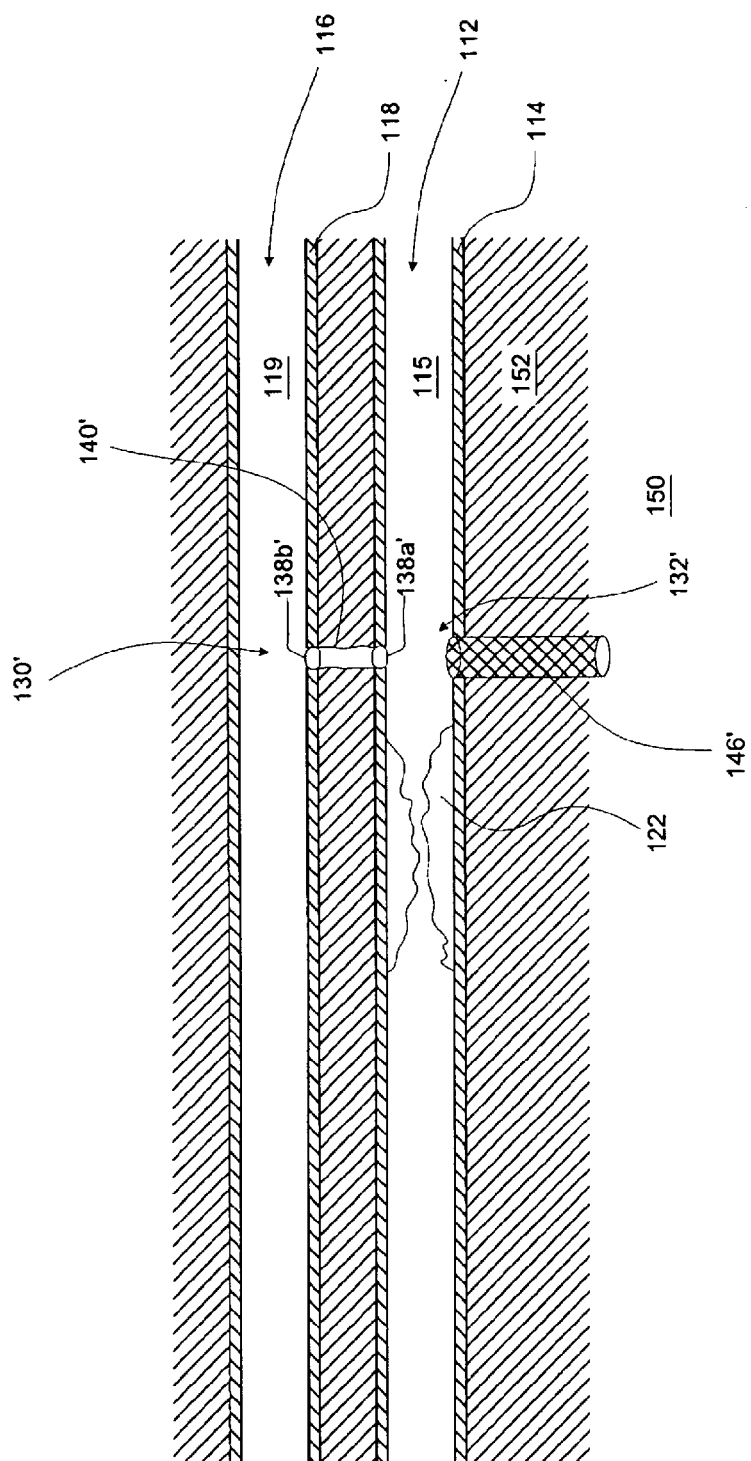

As shown in FIG. 3B, the second location 132' is situated downstream or distal to the obstruction 122. Accordingly, the amount of blood flow through the first coronary vessel 112 (e.g., the coronary artery) is reduced due to the obstruction 122. As discussed above, several methods exist that allow surgeons to treat the diseased blood vessel by supplementing the blood flow through the first coronary vessel 112. In particular, the method of the present disclosure treats the diseased blood vessel by creating a channel that leads directly from a chamber 150 of the heart through the myocardium 152. For example, as shown in FIG. 3C, once the catheter 102 is situated at the second location 132' within the first coronary vessel 112 (e.g., the coronary artery), a channel 143' can be established between the heart chamber 150 and the first coronary vessel 112. In particular, as shown in FIG. 3C and as discussed above, the catheter device 102 can be equipped with (or used in conjunction with a catheter equipped with) an ablation device, for example, an ablation tip (not shown) capable of ablating or otherwise creating the channel 143' between the first coronary vessel 112 and the heart chamber 150.

Once the channel 143' is formed, a transmyocardial implant 146' (e.g., a conduit) can be deployed within the channel 143'. In certain embodiments, the transmyocardial implant 146' can include a tubular reinforcing structure (e.g., a mesh and/or coild tube, a tube defined by a plurality of circumferential and axial struts/supports, etc.) that is expandable from an undeployed state to a deployed state. In the undeployed state, the transmyocardial implant 146' has a reduce diameter sized for allowing the implant to be directed through the patient's 100 vasculature. In the deployed state, the implant has an expanded diameter sized for allowing the transmyocardial implant 146' to be securely held within the channel 143'. The reinforcing structure of the transmyocardial implant 146' can be expanded by known techniques (e.g., the structure can be balloon expandable or self expanding) and can include a liner for preventing thrombosis as discussed above.

During installation, the transmyocardial implant 146' can be positioned within the channel 143' in its undeployed state. Once properly positioned, the transmyocardial implant 146' can be deployed. In it deployed state, the transmyocardial implant 146' is sized to be retained within the formed channel 143'. Moreover, once in place, the transmyocardial implant 146' creates a permanent transmyocardial channel between the heart chamber 150 and the coronary artery 112.

In addition to deployment of the transmyocardial implant 146', the interstitial passageway 140' can be blocked to restore and/or ensure normal coronary aterial and veinous blood flow. To accomplish this, one or more embolization devices can be deployed within the interstitial passageways 140'. In the embodiment illustrated in FIG. 3E, at least two embolization devices are deployed within the interstitial passageway 140'. For example, the embolization device 138a' can be deployed within the first coronary vessel 112 (e.g., the coronary artery) proximate to the wall 114. Similarly, the embolization device 138b' can be deployed within the second coronary vessel 116 (e.g., the coronary vein) proximate to the wall 118. The embolization devices 138a', 138b' can include any device and/or material capable preventing blood flow through the interstitial passageway 140'. For example, the embolization devices 138a', 138b' can include detachable balloons, coils, strands of coagulation producing material, microfibrillar collagen, collagen sponge, cellulose gel or sponge, such as Gelfoam™, surgical glue, such as, Tissel™ or Genzyme™, special stents, or other similar embolization devices.

Still yet another possible method for treating a diseased blood vessel by utilizing the patient's 100 vascular system as a conduit for accessing or reaching a desired location within the patient's body will now be described in connection with FIGS. 4A–4E. In this embodiment, the catheter device 102 is advanced through the patient's 100 (FIG. 1) arterial system into the cardiovascular system 111 (FIG. 1) and is positioned within the first coronary blood vessel 112 (e.g., the coronary artery). The catheter device 102 can be advanced within the patient's 100 vascular system to a first location 130" within the first coronary blood vessel 112 (e.g., the coronary vein). In the illustrated embodiment, the first location 130" is situated proximate to the obstruction 122. As discussed above, it is often desirous to treat the diseased blood vessel (e.g., via revascularization or any other suitable technique or medical intervention) by situating the catheter 102 downstream or distal to the obstruction 122. However, in the embodiment illustrated in FIGS. 4A–4E, the catheter 102 can be positioned at a location downstream or distal to the obstruction 122 by advancing the catheter 102 through the obstruction 122.

As shown in FIG. 4B, the guide wire 103 can be advanced through the obstruction 122 to a second location 132" distal to the obstruction 122. As shown in FIG. 4C, the catheter device 102 can be equipped with (or used in conjunction with a catheter equipped with) a balloon or other similar device capable of mechanically compressing the arteriosclerotic plaque against the wall 114 of the first coronary blood vessel 112 as is commonly understood in the art. In so doing, the amount of blood flow through the first coronary blood vessel 112 can be increased. Furthermore, additional medical devices and/or surgical tools can be advanced to the second location 132" distal to the obstruction 122.

Once the catheter 102 is situated at the second location 132" within the first coronary vessel 112 (e.g., the coronary artery), a channel can be established between the heart chamber 150 and the first coronary vessel 112. In the particular embodiment illustrated in FIGS. 4A–4E, the catheter device 102 can be directed towards the heart chamber 150 using an existing passageway from the first coronary vessel 112. For example, the catheter 102 can be directed towards the heart chamber 150 via a septal opening or branch 160, 162 formed through the wall 114 of the first coronary blood vessel 112. Alternatively, the catheter 102 can form a channel to the heart chamber 150 without advancing through an existing opening.

In situations where an existing opening is used, such as, the septal branches 160, 162, the pathway to the heart chamber 150 must be extended to establish communication with the heart chamber 150. For example, as shown in FIG. 4D, a pathway extension 163 can be formed to complete the path to the heart chamber 150. To accomplish this, the catheter device 102 can be equipped with (or used in conjunction with a catheter equipped with) an ablation device, for example, an ablation tip (not shown) capable of ablating or otherwise creating the channel the pathway extension 163 between either of the septal branches 160, 162 into the heart chamber 150. The existing septal branch 162 and the pathway extension 163 combine to define an interstitial passageway or channel 165 between the first coronary vessel 112 and the heart chamber 150.

As shown in FIG. 4E and as discussed above, once the channel 165 is formed, a transmyocardial implant 166 can be deployed in the channel 165. Additionally, a stent forming device 168 can be deployed within the first coronary blood vessel 112 adjacent to the channel 165. As can be seen in FIG. 4E, the transmyocardial implant 166 and the stent forming device 168 cooperate to create a permanent transmyocardial channel between the heart chamber 150 and the coronary artery 112.

The various embodiments described above are provided by way of illustration only and should not be construed to limit the invention. Those skilled in the art will readily recognize the various modifications and changes which may be made to the present invention without strictly following the exemplary embodiments illustrated and described herein, and without departing from the true spirit and scope of the present invention, which is set forth in the following claims.

The claimed invention is:

1. A method for supplementing a flow of blood to a portion of the cardiovascular system of a patient; the method comprising:
   inserting a catheter device into the vasculature of the patient and advancing the catheter device to a first location within a first coronary vessel within the cardiovascular system; and
   forming a blood flow path from a heart chamber directly to the first coronary vessel via a preexisting natural septal opening extending into the heart wall between the heart chamber and the first coronary vessel.

2. The method according to claim 1, wherein forming a blood flow path from the heart chamber directly to the first coronary vessel includes placing a conduit in a heart wall between the heart chamber and the first coronary vessel.

3. The method according to claim 2, wherein placing a conduit in a heart wall between the heart chamber and the first coronary vessel includes placing a conduit in the preexisting natural septal opening.

4. The method according to claim 1, wherein the first coronary vessel is a coronary artery.

5. The method according to claim 4, wherein the coronary artery is a left anterior descending coronary artery.

6. The method according to claim 1, further comprising
   advancing the catheter device to a second location within a second coronary vessel within the cardiovascular system; and
   guiding the catheter device through an interstitial passageway formed between the first location and the second location,
   wherein the first location within the first coronary vessel is distal to an obstruction in the first coronary vessel.

7. The method according to claim 6, wherein the interstitial passageway is formed through a wall of the first coronary vessel and through a wall of the second coronary vessel between the first and second locations.

8. The method according to claim 6, further comprising occluding the interstitial passageway between the first coronary vessel and the second coronary vessel to prevent blood flow through the interstitial passageway.

9. The method according to claim 8, wherein occluding the interstitial passageway includes deploying an embolization substance at a wall of the first vessel and at a wall of the second vessel.

10. The method according to claim 8, wherein occluding the interstitial passageway includes deploying an embolization device within the interstitial passageway.

11. The method according to claim 6, wherein the second coronary vessel is a coronary vein proximate to the coronary artery.

12. The method according to claim 11, wherein the second coronary vessel is a great cardiac vein.

13. The method according to claim 1, further comprising
   guiding the catheter device through a first interstitial passageway formed between the first location and a second location within a second coronary vessel within the cardiovascular system;
   advancing the catheter device to a third location within the second coronary vessel; and
   guiding the catheter device through a second interstitial passageway formed between the third location and a fourth location within the first coronary vessel, the fourth location being distal to an obstruction in the first coronary vessel.

14. The method according to claim 13, wherein:
   the first interstitial passageway is formed through a wall of the first coronary vessel and through a wall of the second coronary vessel between the first and second locations; and
   the second interstitial passageway is formed through a wall of the second coronary vessel and through a wall of the first coronary vessel between the third and fourth locations.

15. The method according to claim 13, further comprising occluding the first and second interstitial passageways between the first coronary vessel and the second coronary vessel to prevent blood flow through either of the first or second passageways.

16. The method according to claim 15, wherein occluding the first and second interstitial passageways includes deploying an embolization device within each of the first and second passageways.

17. The method according to claim 15, wherein occluding the first and second interstitial passageways includes:
   deploying an embolization substance at a wall of the first coronary vessel and at a wall of the second coronary vessel at the first interstitial passageway; and
   deploying an embolization substance at a wall of the first coronary vessel and at a wall of the second coronary vessel at the second interstitial passageway.

18. The method according to claim 13, wherein the first coronary vessel is a coronary artery.

19. The method according to claim 18, wherein the second coronary vessel is a coronary vein proximate to the coronary artery.

20. The method according to claim 19, wherein the first coronary vessel is a great cardiac vein.

21. The method according to claim 18, wherein the coronary artery is a left anterior descending coronary artery.

22. A method for supplementing a flow of blood to a portion of the cardiovascular system of a patient, the method comprising:
   (a) inserting a catheter device into the vasculature of the patient and advancing the catheter device to a first location within a coronary vessel within the cardiovascular system, the first location being proximate to an obstruction within the coronary vessel;

(b) advancing the catheter device through the obstruction to a second position distal to the obstruction;

(c) guiding the catheter device through an interstitial passageway extending into a heart wall between a heart chamber and the coronary vessel; and (d) placing a conduit in the interstitial passageway extending into the heart wall between the heart chamber and the coronary vessel, wherein the interstitial passageway includes a preexisting natural septal opening extending into the heart wall between the heart chamber and the coronary vessel.

23. The method according to claim 22, wherein the coronary vessel is a coronary artery.

24. The method according to claim 22 further comprising distending the obstruction within the coronary vessel.

25. The method according to claim 24, wherein distending the obstruction within the coronary vessel includes inflating a balloon at the obstruction within the coronary vessel.

* * * * *

UNITED STATES PATENT AND TRADEMARK OFFICE
CERTIFICATE OF CORRECTION

PATENT NO.    : 6,976,990 B2
DATED         : December 20, 2005
INVENTOR(S)   : David H. Mowry It is certified that error appears in the above-identified patent and that said Letters Patent is hereby corrected as shown below:

Column 11,
Line 33, "patient; the" should read -- patient, the --.

Signed and Sealed this

Twenty-first Day of February, 2006

JON W. DUDAS
*Director of the United States Patent and Trademark Office*